United States Patent [19]

Harris et al.

[11] 3,995,259

[45] Nov. 30, 1976

[54] METHOD FOR DISPLAYING DIGITAL ELECTRONIC DATA DIFFERENTLY REPRESENTATIVE OF CERTAIN EVENTS

[75] Inventors: George Jerry Harris, Framingham; Donald DePedro, Millis, both of Mass.

[73] Assignee: American Optical Corporation, Southbridge, Mass.

[22] Filed: July 2, 1975

[21] Appl. No.: 592,709

Related U.S. Application Data

[62] Division of Ser. No. 335,631, Feb. 26, 1973, Pat. No. 3,909,792.

[52] U.S. Cl. .................. 340/172.5; 340/324 AD; 128/2.06 A

[51] Int. Cl.² .................. G06F 3/00; A61B 5/02; G06F 3/14; G06F 13/00

[58] Field of Search ...... 340/172.5, 324 A, 324 AD; 128/2.06 A

[56] References Cited

UNITED STATES PATENTS

| | | | |
|---|---|---|---|
| 3,522,597 | 8/1970 | Murphy | 340/324 |
| 3,637,997 | 1/1972 | Petersen | 340/324 |
| 3,829,841 | 8/1974 | Steinberg | 340/172.5 |

*Primary Examiner*—Gareth D. Shaw
*Assistant Examiner*—James D. Thomas
*Attorney, Agent, or Firm*—Stephen A. Schneeberger; William C. Nealon; H. R. Berkenstock, Jr.

[57] ABSTRACT

There is disclosed an electrocardiographic review system for displaying ECG data for each of eight patients. Whenever the data for a new patient is to be observed, two trend plots are first displayed on the screen. One of these represents the number of heartbeats per minute and the other represents the number of ectopic beats per minute, the time axis being divided into approximately 240 discrete 1-minute intervals so that the trend data for a 4-hour monitoring period can be displayed. The reviewing physician can move a cursor across the screen to a point of particular interest, for example, to a point along the time axis corresponding to a 1-minute interval during which many ectopic beats were detected. Following this, when a display key in the system is operated, a four-second stationary display of the first ECG waveform of interest which occurred during that 1-minute interval is formed. Thereafter, each operation of the display key controls the display of another 4-second ECG waveform. In this manner, the reviewing physician can determine those intervals during monitoring which are of particular interest, and can then immediately control the display of the successive 4-second ECG waveforms on the screen. The same screen is thus used to display both compressed-time trend data, and expanded-time ECG waveforms.

2 Claims, 27 Drawing Figures

LOAD ECT
LOAD HR
S4
S3
S2
3-BIT COUNTER
FF3
1-μSEC ONE SHOT
FF1
FF2
FF4
1-μSEC ONE SHOT
PULSER
8-BIT COUNTER
ENCODER
CP8
CP1
CLR
CP1-8
WT CLK
WT DATA(1) H
FORCE 2
FORCE 3
1-μSEC ONE SHOT
OUT 13
OUT 14
OUT 15
NDR
DIR
REQA
IN 0
IN 1
IN 3
IN 4
IN 5
IN 6
IN 13
TO DR11-A GENERAL PURPOSE INTERFACE
D
R
C
P1
P8
TO KEYBOARD 19
WRITE
WT CLK
WT DATA(1) H
TO DISPLAY INTERFACE 17

1024 KHZ
SWEEP SYNC
128 KHZ
2048 KHZ
ECG
ECG CLK
MSG
MSG CLK
ECT
ECT CLK
HR
HR CLK
CPI-8
256-BIT SHIFT REGISTER
3840-BIT SHIFT REGISTER (ECG)
2048-BIT SHIFT REGISTER (ECT)
2048-BIT SHIFT REGISTER (HR)
FF5A
FF5B
SWEEP SYNC
LOAD ECT
LOAD HR
S4
S3
S2
WT CLK
WT DATA (I) H

128 KHZ
BYTE SYNC
CLR
1024 KHZ
2048 KHZ
128 KHZ
-ECG ANLG
-HR ANLG
4096 KHZ
SWEEP SYNC
MSG
MSG CLK
ECT
ECT CLK
CPI-8
161
LOAD
BYTE SYNC 2
144
100-NSEC ONE SHOT
8-BIT D/A CONVERTER
8-BIT LATCH
8-BIT SHIFT REGISTER
HR CLK
FF8
-ECG ANLG
158
159
160
154
157
172
143
142
3-BIT COUNTER
CLR
155
156
.5 KHZ
141
100-NSEC ONE SHOT
128 KHZ
2048 KHZ
10-μSEC ONE SHOT
140
151
152
153
ECG CLK
1024 KHZ
4096 KHZ
SWEEP SYNC
2048 KHZ
ECG
ECG CLK
MSG
ECT
HR
HR CLK

MSG GATE
HOR SWEEP
128 KHZ
BYTE SYNC3
100-NSEC ONE SHOT
174
1024 KHZ
2048 KHZ
-Y
176
ECT VIDEO
165
MSG CLK
MSG
SWEEP SYNC
CPI-8
FF10
149
3-BIT COUNTER
148
CLR
173
169
170
171
FF11
BORROW
175
163
COUNTDOWN
5-BIT U/D COUNTER
8-BIT SHIFT REGISTER
ECT CLK
-STAIRCASE
166
167
168
LOAD
ECT GATE
147
BYTE SYNC1
RESET BAR
FF9
162
146
145
HR GATE
178
GATE
177
ECG GATE
128 KHZ
BYTE SYNC1
CLR
1024 KHZ
2048 KHZ
128 KHZ
-ECG ANLG
-HR ANLG
4096 KHZ
SWEEP SYNC
MSG
MSG CLK
ECT
ECT CLK
CPI-8

+Y
HR GATE
ECG GATE
SWEEP SYNC
BLIP
CPI-8
RESET RASTER
EMITTER FOLLOWER
TO OSCILLOSCOPE
Z
+Y
HOR SWEEP
-Y
MSG VIDEO
STROBE
3-BIT COUNTER
CLR
8-LINE SELECTOR TI-74151
ROM SIGNETICS 2516
8-BIT LATCH
8-BIT SHIFT REGISTER
CLK
LOAD
FF12
FF13
MSG GATE
HOR SWEEP
128 KHZ
BYTE SYNC3
1024 KHZ
2048 KHZ
-Y
ECT VIDEO
MSG CLK
MSG SWEEP SYNC
CPI-8

100
4096-KHZ OSCILLATOR
101
1-BIT COUNTER
102
1-BIT COUNTER
103
2-BIT COUNTER
104
1-BIT COUNTER
105
8-BIT COUNTER
1-μSEC ONE SHOT
108
1-BIT LATCH
LOAD 109
1-μSEC ONE SHOT
111
8-BIT LATCH
112
LOAD
113
LSB
LSB+1 MSB
D/A CONVERTER
9-BIT D/A CONVERTER
114
HOR SWEEP
ECG GATE
4096 KHZ
1024 KHZ
2048 KHZ
128 KHZ
.5 KHZ
128 KHZ 106
3-BIT COUNTER
B1
B2
B4
114
114
114
B1
B2
B4
117
118
119
120
121
122
123
S
FF7
R
1
0
S
FF6
R
1
0
HR GATE
CURSOR GATE
ECG GATE
ECT GATE
MSG GATE
R
R/2
R/3
R/4
R
R/2
R/2
STAIRCASE
HOR SWEEP
MSG GATE
ECT GATE
RESET BAR
HR GATE
ECG GATE
HR GATE
CURSOR GATE
ECG GATE
MSG GATE
RESET BAR
ECT GATE
128 KHZ
HOR SWEEP
ECG GATE
128 KHZ

F/G. 11
+V
216
T4
T2
T1
T3
220
CLR
8-BIT COUNTER
201
8-BIT COMPARATOR
200
EQUAL
40-μ/SEC ONE SHOT
204
BLIP
STROBE
1-μ/SEC ONE SHOT
217
202
209
205
206
207
208
218
HR GATE
ECG GATE
SWEEP SYNC
BLIP
CPI-8
RESET RASTER
HR GATE
CURSOR GATE
ECG GATE
MSG GATE
RESET BAR
ECT GATE
128 KHZ

| | | FIG. 9 | FIG. 10 | FIG. 11 |
|---|---|---|---|---|
| FIG. 4 | FIG. 5 | FIG. 6 | FIG. 7 | FIG. 8 |
FIG. 12
| FF1 | FF2 | STATE NUMBER | OPERATION |
|---|---|---|---|
| 0 | 0 | S1 | IDLE |
| 1 | 0 | S2 | TREND LOAD |
| 1 | 1 | S3 | ECG LOAD |
| 0 | 1 | S4 | DISPLAY |
FIG. 13
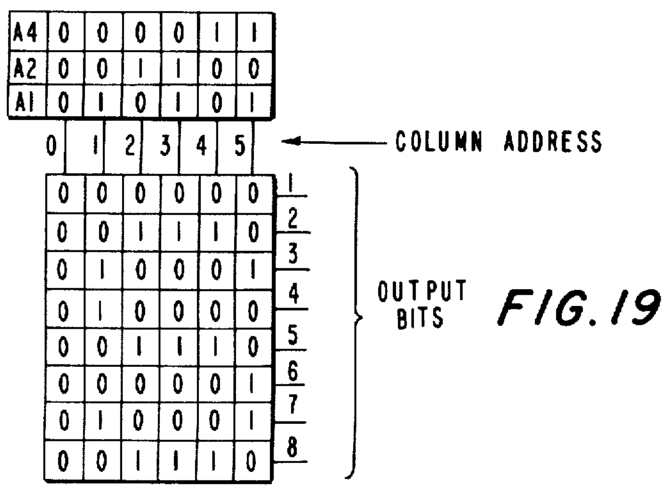
| | 0 | 1 | 2 | 3 | 4 | 5 |
|---|---|---|---|---|---|---|
| A4 | 0 | 0 | 0 | 0 | 1 | 1 |
| A2 | 0 | 0 | 1 | 1 | 0 | 0 |
| A1 | 0 | 1 | 0 | 1 | 0 | 1 |
| 1 | 0 | 0 | 0 | 0 | 0 | 0 |
| 2 | 0 | 0 | 1 | 1 | 1 | 0 |
| 3 | 0 | 1 | 0 | 0 | 0 | 1 |
| 4 | 0 | 1 | 0 | 0 | 0 | 0 |
| 5 | 0 | 0 | 1 | 1 | 1 | 0 |
| 6 | 0 | 0 | 0 | 0 | 0 | 1 |
| 7 | 0 | 1 | 0 | 0 | 0 | 1 |
| 8 | 0 | 0 | 1 | 1 | 1 | 0 |
FIG. 19
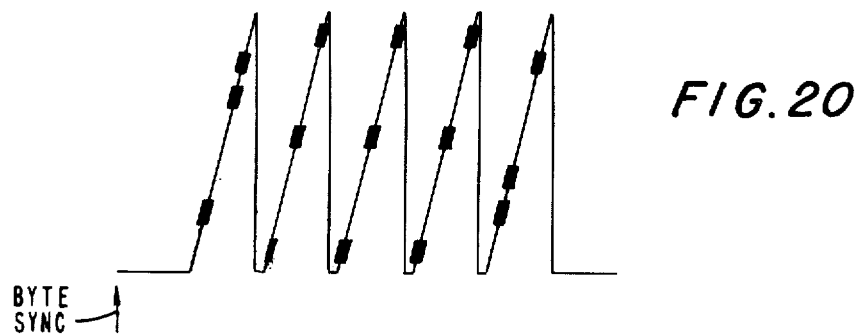
FIG. 20

| SWEEP TYPE | NO. OF REQUIRED CLOCK PULSES DURING 2-MSEC SWEEP | CLOCK RATE |
|---|---|---|
| MSG | 256 | 128 KHZ |
| ECG | 4096 | 2048 KHZ |
| CURSOR | 256 | 128 KHZ |
| HR | 2048 | 1024 KHZ |
| ECT | 2048 | 1024 KHZ |

2048 KHZ
COUNTER 142 CHANGES STATE
GATE 143 (J INPUT OF FF8)
FF8
BYTE SYNC2

F1, F2, F4 CHANGE
1024 KHZ
2048 KHZ
GATE 232
GATE 231
FF13
RESET RASTER
GATE 234

BYTE SYNC3
128 KHZ
A1
A2
A3
1024 KHZ
F1
F2
F4
GATE 248
GATE
GATE 264
FF12
RESET RASTER
RASTER RAMP (WITH MSG GATE ON)
0
1
2
3
4
5
6
7
0
1
0

FIG. 21A
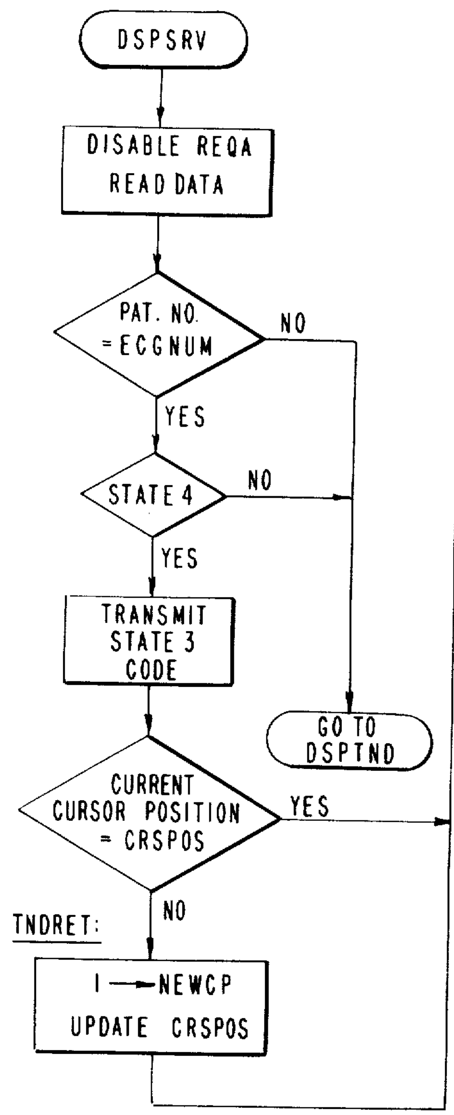
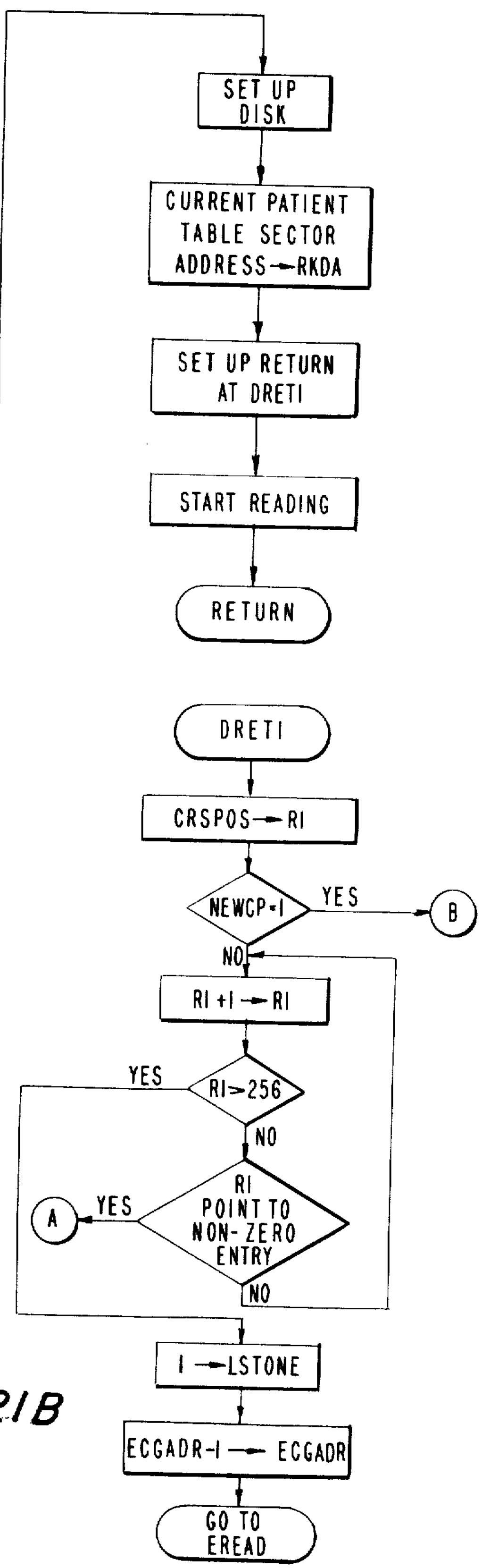
FIG. 21B

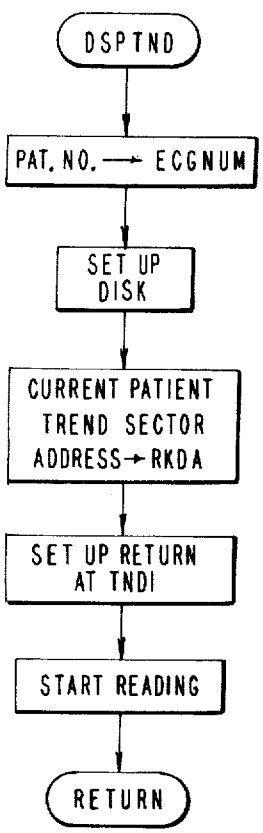
FIG. 23A
FIG. 24
PATIENT TABLE SECTOR
| ADDRESS WITHIN SECTOR N+1 | STORED DATA (ADDRESS OF ECG DATA SECTOR) |
|---|---|
| 1 | 0 |
| 2 | N+2 |
| 3 | N+3 |
| 4 | N+5 |
| 5 | 0 |
| 6 | 0 |
| 7 | N+9 |
| 8 | N+12 |
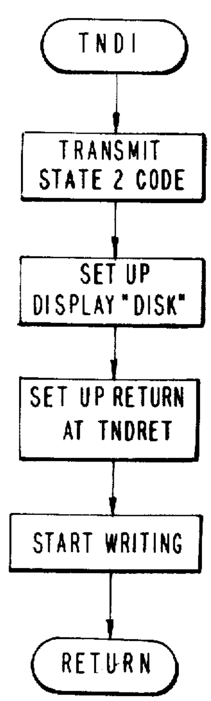
FIG. 23B
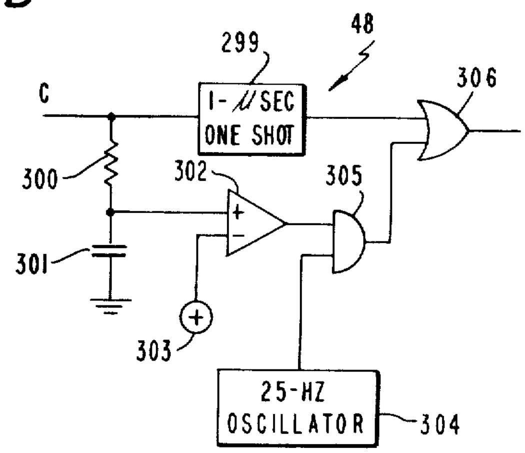
FIG. 4A

METHOD FOR DISPLAYING DIGITAL ELECTRONIC DATA DIFFERENTLY REPRESENTATIVE OF CERTAIN EVENTS

This is a division of application Ser. No. 335,631, filed Feb. 26, 1973, and now U.S. Pat. No. 3,909,792 issued Sept. 30, 1975.

TABLE OF CONTENTS

| Subheading | Columns |
|---|---|
| Description of Prior Art | 1 |
| Brief Description of the Invention | 2 |
| The Drawings | 4 |
| The Display and the Keyboard | 5 |
| The Overall System | 7 |
| The Computer | 7 |
| The Keyboard | 8 |
| The Disk Interface | 10 |
| The Display Interface | 10 |
| The Display and Keyboard Logic | 11 |
| The System States | 14 |
| Packing of Trend Data | 15 |
| CRT Refresh Memory | 16 |
| ECG Data Loading | 17 |
| Recirculation & Display | 18 |
| Reloading ECG Data | 20 |
| The 4-Channel Display | 20 |
| a) CRT Sweep Waveforms | 21 |
| b) System Clock | 22 |
| c) Analog Display Generation | 22 |
| d) Sequencing of Horizontal Sweeps | 22 |
| e) Vertical Sweeps | 24 |
| The Digital to Analog Conversion | 25 |
| The CRT Blanking | 29 |
| The Detailed Message Generation | 32 |
| Organization of Data and its Orderly Transmission to the Display and Keyboard Logic | 37 |
| The Disk Storage | 37 |
| The Display Service | 39 |
| a) Trend Display | 40 |
| b) ECG Display | 40 |
| c) Table Lookup | 40 |
| d) Filled Disk | 44 |
| e) Reading ECG Data from Disk | 44 |
| f) Sending ECG Data to Display | 45 |
| g) Reading Trend from Disk | 46 |
| h) Trend to Display | 46 |
| Recording Sequence | 46 |
| Alternative Embodiments of the Invention | 48 |

This invention relates to display systems, and more particularly to display systems which facilitate the review of electrocardiographic and other signals.

DESCRIPTION OF PRIOR ART

The conventional ECG paper trace serves admirably when a patient is being tested and a physician must review a relatively limited number of waveforms. But when a patient is being monitored continuously, for example, in the intensive care unit of a hospital, the paper trace form of recording has a severe limitation. For example, if a physician reviews the patient's progress at 4-hour intervals, and if he must review a 4-hour paper trace at such a time, it is apparent that the task is indeed formidable.

For this reason, various systems have been devised for reducing the amount of information which is recorded during an extended monitoring interval. Two such systems are disclosed in U.S. Pat. No. 3,616,791 issued on Nov. 2, 1971 to George J. Harris and entitled "ELECTRO-CARDIOGRAPHIC MORPHOLOGY RECOGNITION SYSTEM", and copending application Ser. No. 192,191 of George J. Harris, filed on Oct. 26, 1971 issued on Apr. 30, 1974 as U.S. Pat. No. 3,807,392, and entitled "ELECTRO-CARDIOGRAPHIC PATIENT MONITORING AND MORPHOLOGY RECOGNITION METHOD". The systems disclosed in the aforesaid patent and application detect ectopic beats and other atypical waveforms; in response to the detection of any such beat or waveform, a 4-second recording of the patient's ECG signal is made. The 4-second recording includes a portion of the ECG signal which preceded the detection of an ectopic or other unusual beat, and a portion of the signal which follows it.

But even this approach has been found to present problems in connection with the review of the recording. It is exceedingly difficult for the reviewing physician to get a "bird's-eye" view of the overall cardiac activity during the extended monitoring time period. Moreover, if there is a limited time interval of special interest to the physician, and for which he wishes to review the individual ECG waveforms which have been recorded, it may be difficult for him to isolate and retrieve those particular waveforms.

BRIEF DESCRIPTION OF THE INVENTION

It is a general object of our invention to provide an improved display system for facilitating the review of electrocardiographic and other sets of data.

In accordance with the principles of the present invention, an electronic display is provided in which the physician has control over what is displayed. In the illustrative embodiment of the invention, there are provided recorded signals for each of eight different patients. The physician can select for display the data for a particular patient, and he can also control the particular data for that patient which is displayed. The form of the display is an important aspect of the invention because it is this which greatly aids a physician in the review of ECG waveforms recorded over extended time periods and permits him to select particular waveforms of interest and to control their immediate display. But before proceeding to a description of the form of the display, it is necessary to understand the four types of data recorded for each patient. No claim to invention is being made herein to the derivation and recording of the four types of signals. The invention pertains to the display of the signals and the manner in which the display can be controlled by the reviewing physician.

The first type of data which is stored for review is heartbeat rate "trend" data. The number of heartbeats detected during each one-minute interval of monitoring is recorded. The second type of data which is recorded is ectopic beat rate "trend" data. Utilizing equipment such as that disclosed in the two aforesaid systems, a count is maintained for each one-minute interval of the number of ectopic beats which occur. For each of the 240 minutes in a 4-hour monitoring period, there is thus available a count of the number of heartbeats and the number of ectopic beats which took place during that minute.

The third type of data which is recorded is electrocardiograhic signal data for each patient. Whenever an ectopic beat is detected, a 4-second ECG signal segment is recorded. The recording is in the form of sampled data. If samples of an ECG signal are taken at the rate of 120 per second, the signal can be reconstructed with no loss of fidelity. A set of 480 samples is recorded for each 4-second signal segment whenever an ectopic beat is detected.

The fourth type of data which is recorded is message data; a message is associated with each 4-second ECG signal recording. The message includes a patient identiication number, the time of day when the recording was made and a short description of the type of beat recorded, for example, a ventricular premature beat (VPB). (The two systems referred to above are capable of analyzing and characterizing heartbeats.)

The display utilizes an oscilloscope, and the sweep circuitry is arranged such that there are four types of horizontal sweeps across the face of the tube. For each type of horizontal sweep, the vertical sweep is modulated at a fast rate to control a respective one of four different displays. The lowest display is of ectopic beat rate data. The horizontal axis of the display represents a 4-hour time period. For the lowest display, the vertical axis represents ectopic beat rate. For each of the 240 minutes represented along the time axis, a vertical bar is drawn on the face of the oscilloscope, the height of the bar representing the number of ectopic beats detected during the respective minute. There is thus formed a histogram which is a "bird's-eye" view or "compressed-time" trend plot of the 4-hour monitoring period insofar as ectopic beat rate is concerned.

Immediately above this histogram there is displayed a plot which represents the same patient's heartbeat rate over the same 4-hour period. For each of the 240 minutes represented in the display, a single dot is formed on the display, the 240 dots appearing as a continuous curve across the face of the display. There is thus available a "bird's-eye" or trend view of the patient's heartbeat rate over the extended monitoring period.

Above the heartbeat rate plot, a 4-second "expanded-time" ECG signal segment is displayed. The display is stationary so that it can be reviewed by the physician. It is not possible to display simultaneously all of the 4-second recordings which were taken during the 4-hour monitoring period. A key aspect of our invention pertains to the manner in which the reviewing physician can select particular 4-second segments for display. Immediately above a selected 4-second displayed segment there appears an associated message — patient number, time of day, and characterization of the ectopic beat which triggered the 4-second recording in the first place.

There is also displayed a cursor, or mark, directly above the heartbeat rate plot. The physician is provided with a key which when operated moves the cursor horizontally, in the direction of increasing time. Each operation of the key causes the cursor to move to the right by the amount of corresponding to one minute in the 4-hour two lower displays. By moving the cursor, the physician in effect selects a particular one of the 240 minutes along the two 4-hour trend plots. Typically, the physician will look at the two compressed-time displays (ectopic beat and heartbeat rates) and selects a time of day during which there was a type of heart activity of particular interest. For example, the physician may move the cursor across the display until it is directly above a peak in either of the compressed-time trend plots. The equipment is provided with a "display" key which when operated by the physician controls the display of a 4-second ECG signal segment. After the cursor is moved to a new position (corresponding to a new minute in the 4-hour monitoring period), if the display key is operated the 4-second ECG signal segment which is immediately displayed is the first such segment which was recorded during the selected minute. After examining this segment, if the physician again operates the display button, the next 4-second ECG signal segment is displayed. In this manner, the physician can display successive 4-second segments which were recorded during any minute of interest. Theoretically, there may be up to 15 such segments which were recorded during any one-minute monitoring interval.

Should the physician keep on operating the display button, successive 4-second segments of the ECG signal would be displayed. After all of the segments recorded for any one-minute interval have been displayed in this manner, the first segment, if any, recorded during the next minute interval will be displayed. In this case, the cursor automatically moves over one position, corresponding to one minute on the two compressed-time plots, to indicate that the 4-second ECG signal segment which is being displayed was taken during the next minute of the 4-hour monitoring period.

The major advantage of the display system of our invention is that the physician is provided with at least one compressed-time plot (it is not necessary in a less sophisticated system to display both heartbeat and ectopic beat rate plots) from which he can immediately perceive the overall activity during the extended monitoring period. Based on the compressed-time plot or plots, the physician can select a particular time of day which is of interest by manually controlling movement of the cursor across the face of the display. After the cursor has been moved to the selected time of day, the physician can then control the successive displays of the individual 4-second ECG signal segments which were recorded during the respective one-minute interval. The physician can thus quickly retrieve and have displayed for him all of the ECG signal segments which are of particular interest to him, that is, all of those ECG signal segments which occurred during one-minute intervals when there was heartbeat or ectopic beat activity of particular interest. The physician cannot only select those ECG signal segments which he wants to see based upon information represented in the compressed-time plots, but the first such ECG signal segment is displayed immediately once a particular time of day is selected and successive ECG signal segments are displayed automatically simply by operating the display key.

Further objects, features and advantages of our invention will become apparent upon consideration of the following detailed description in conjunction with the drawing, in which:

THE DRAWINGS

FIG. 12 represents the manner in which FIGS. 4–11 are to be arranged;

FIG. 13 is a state diagram which will be helpful in understanding the operation of the display and keyboard logic and, in particular, the circuitry on FIG. 4;

FIG. 19 depicts the operation of read only memory (ROM) 240 of FIG. 8;

FIG. 20 depicts the manner in which a character in the display message is formed and will be helpful in understanding the operation of 8-line selector 241 of FIG. 8;

FIGS. 21–23 represent the steps for controlling the transmission of data to the display and keyboard logic in the preferred embodiment of the invention (the present invention is a display system — the computer of FIG. 1 serves primarily to furnish data to the display and keyboard logic and is the most cost-effective way to accomplish this function, although it will be apparent to those skilled in the art that conventional core or semiconductor memories can be used in lieu of a disk drive and a computer); and FIG. 24 depicts the manner in which data for each patient is organized on a disk used in the system.

THE DISPLAY AND THE KEYBOARD

Figure 1:
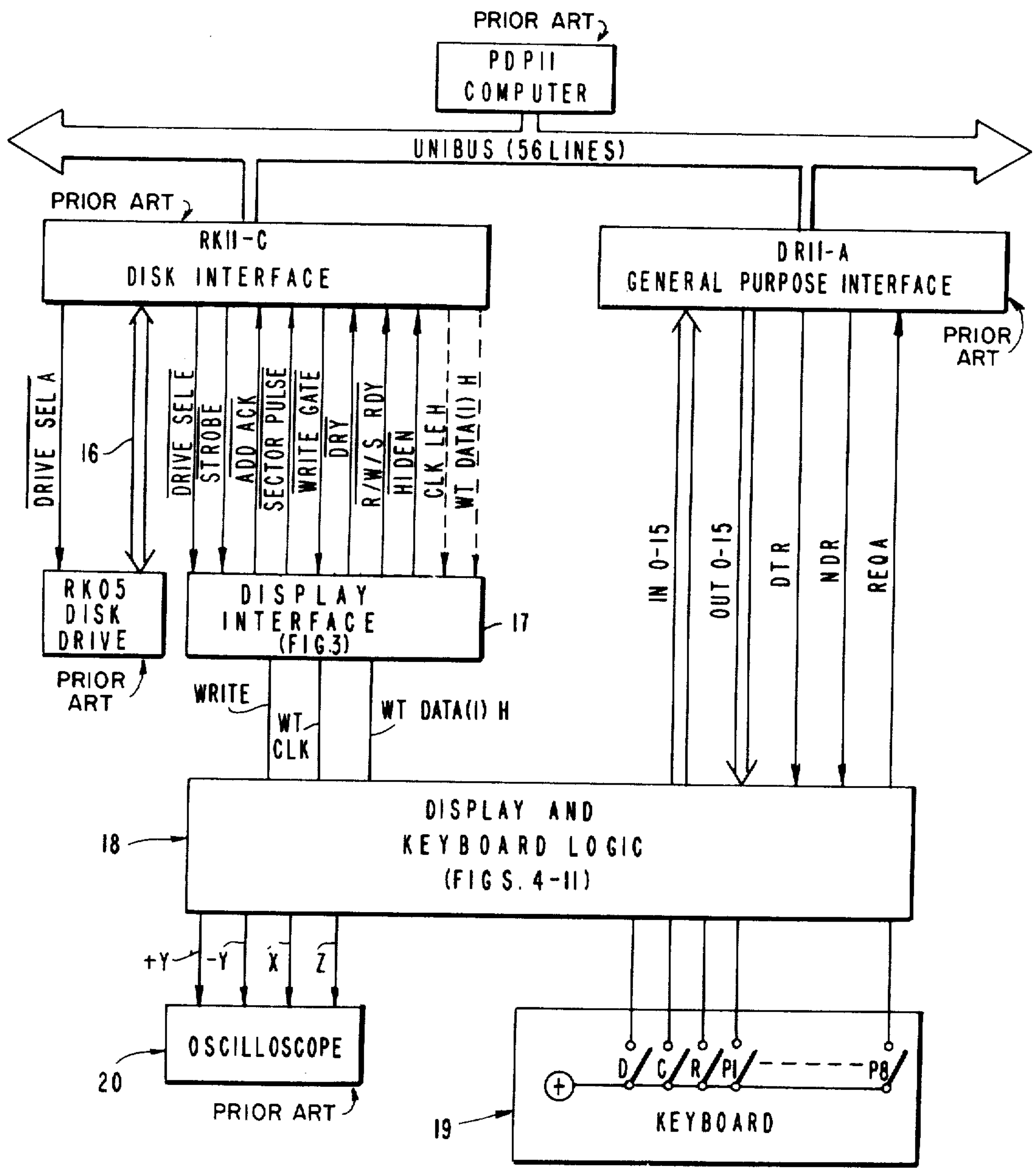
FIG. 1 depicts a block diagram of the system of my invention.
Figure 2:
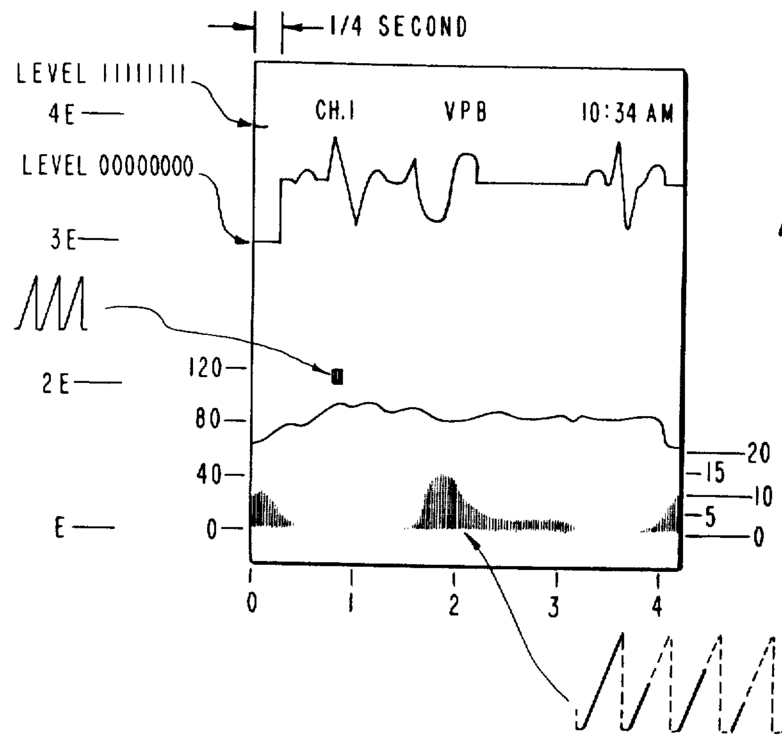
FIG. 2 depicts the form of the display.

Before proceeding to a description of the block-diagram system of FIG. 1, it will be helpful to note the form of the display shown in FIG. 2. The lowest display is a histogram repesenting ectopic beat rate. The horizontal (time) axis of the display is labeled in increments repesenting both hours (for the two trend plots) and seconds (for the ECG waveform which is displayed). For each of the 256 minutes represented, there is a vertical bar whose height represents the number of ectopic beats which occurred during the respective one-minute interval. On the right side of the display the vertical axis is labeled with the number of ectopic beats per minute. (Although 240-minute plots were described above, ectopic beat and heartbeat rate data is available for each of 256 minutes in the illustrative embodiment of the invention. References below to 4-hour plots are to be understood as references to 4-hour, 16-minute plots.)

Immediately above the ectopic beat rate histogram there is a plot which depicts the patient's heartbeat rate over the same 4-hour period. Along the left side of the display, the vertical scale is labeled 0–120 to represent the heartbeat rate.

These two plots give the physician a "bird's-eye" view of the patient's history over an entire 4-hour period. From these two trend plots, nothing can be determined about the detailed shapes of particular ECG waveforms; however, by means of these two displays the physician can immediately ascertain certain trend information about a patient and he can determine particular times of day when the ECG waveform segments which were recorded deserve detailed study.

Directly above the heartbeat rate plot there is displayed a cursor. As shown, the cursor is slightly before the 1-hour mark on the time axis. A cursor key on the system keyboard controls movement of the cursor to the right along the time axis. Whenever the key is operated, the cursor moves one position to the right, corresponding to a one-minute increment. If the cursor key is kept operated, the cursor moves continuously to the right until the key is released. The cursor itself is comprised of several vertical sweeps as shown in the "blow-up" on the left of FIG. 2. However, the sawtooth waveform is so compressed on the display that the cursor appears as a solid mark. Similarly, as shown at the bottom of FIG. 2, the ectopic beat rate histogram also consists of a series of raster sweeps (dotted lines), the height of the visible portion (solid line) of each sweep representing the number of ectopic beats detected during a respective one-minute monitoring interval. Because the sweeps are compressed in the horizontal direction of the display, the form of the lower display is a "solid" histogram.

Above the cursor there is displayed an ECG waveform. The first ¼ second of the waveform is blanked for reasons which will become apparent upon a consideration of the detailed circuitry for controlling the display. The ECG waveform which is thus displayed is actually slightly shorter than that which occurred over a 4-second interval. The ECG waveform data is stored in the form of samples and, as depicted in FIG. 2, the lowest level is represented by sample 00000000 and the peak magnitude is represented by sample 11111111. Directly above the ECG waveform there is a three-part message. The first part is a channel number (in this case, channel 1) which identifies one of eight patients. The second part of the message characterizes the waveform; in the example shown, the waveform is a ventricular premature beat. The third part of the message identifies the time of day when the displayed ECG signal occurred, in this case at 10:34 A.M. This time of day corresponds to the position of the cursor on the display. The time axis is in relative hours and the displayed message informs the physician of the precise time of day when a displayed signal occurred.

Also shown on FIG. 2 are four voltage levels E, 2E, 3E and 4E. These voltage levels, as will be described below, are the respective base voltage levels for the vertical deflecting waveforms for the five horizontal sweeps during which the various displays are formed. (The lowest level E is used to control displays of the heartbeat and ectopic beat rate plots, level 2E is used to control display of the cursor, level 3E is used to control display of an approximately 4-second ECG signal, and level 4E is used to control display of the associated message.)

It is important to note that the expanded-time ECG signal waveform display is different from the two compressed-time trend displays. In other words, the waveform which is displayed is not contained within the trend displays. There are oscilloscopes on the market which are used for the analysis of electrical signals; there is shown on a first channel an expanded display of a small portion of a compressed display on a second channel. The object of our invention is not to show an expanded portion of interest in a compressed time-varying signal. Instead, the object of our invention is to display trend information on at least one channel, and then to display completely different information on another channel, a cursor being moved along the trend display in order to select a particular time of day for identifying the expanded signal which is to be displayed. Very little would be gained simply by providing an expanded plot of the trend data. The advantages of our invention are realized by displaying completely different information in the expanded-time display and using the compressed-time display to select an expanded signal of interest.

As shown on FIG. 1, keyboard 19 of the system includes eleven keys. Keys P1-P8 represent eight different patients. Depending upon which of these keys is operated, the "trend" data, namely, the ectopic beat and heartbeat rate plots for a particular patient are displayed. The reset (R) key simply resets the circuitry in the display and keyboard logic. Typically, this key is operated after the system is first turned on for initialization purposes. The cursor (C) key controls movement of the cursor to the right across the screen. (After the cursor is moved all the way to the right edge of the screen, it appears at the left edge once again.) The display (D) key, when operated, controls the display of a new ECG signal segment at the top of the screen. After the cursor is moved to a new position, the display key must be operated in order for the first ECG signal segment in the new minute of interest (represented by the cursor position) to be displayed. Thereafter, each time that the display key is operated, the next ECG signal segment taken during the same minute of interest is displayed. If the physician keeps on operating the display key until all ECG signal segments in the minute of interest have been displayed, the first ECG signal segment in the next minute during which a segment was recorded (this "next" minute may be several minutes away if ectopic beats were not detected for several minutes) will be displayed. In such a case, the cursor automatically moves to the right the correct number of positions to indicate that the currently displayed ECG signal segment was recorded during a different minute interval.

The Overall System

FIG. 1 is a block-diagram representation of the overall system of my invention. The main blocks insofar as the present invention is concerned are oscilloscope 20, keyboard 19 and display and keyboard logic 18 (FIGS. 4-11). There is a great deal of data which must be stored in order to allow the physician to control the display of signals taken over a 4-hour period for each of eight different patients. The data could be stored in a core, semiconductor or other type of memory coupled directly to the display and keyboard logic. By using conventional addressing circuits, the particular data needed for any display could be retrieved from the memory and operated upon directly by the display and keyboard logic. But this might be quite costly. Instead, in the preferred embodiment of the invention, the data is stored on a magnetic disk. The information is retrieved by a computer and then forwarded to the display and keyboard logic in a conventional fashion. The main function of the computer is to forward data to the display and keyboard logic when it is needed.

The Computer

A preferred computer is the PDP11 manufactured by Digital EQuipment Corporation, the specific description of this computer being presented in Digital Equipment Corporation Publication No. DEC 11-HR2B-D (1970, 1971). A system constructed around such a computer is provided with a 56-line bus, known as a Unibus. In order to interface the computer via the Unibus to peripheral equipment, Digital Equipment Corporation provides several different types of interfaces. One of these is the RK11-C disk interface shown in FIG. 1 for allowing communication with an RKO5 disk drive. The detailed description for the RK11-C disk interface is presented in Digital Equipment Corporation Publication No. DEC-11-HRKA-D, published in 1971; the detailed description of the RKO5 disk drive is presented in Digital Equipment Corporation Publication No. B-DD-RKO5-0, published in 1972. (The trend and ECG data operated upon by the display and keyboard logic of FIGS. 4-11 is stored on a disk in the disk drive.) The DR11-A general purpose interface is a unit which allows the computer to communicate via the Unibus with peripheral equipment in general, in the case of FIG. 1 the display and keyboard logic of FIGS. 4-11.

The DR11-A general purpose interface is described in detail in Digital EQuipment Corporation Publication No. D-CS-M786-0-1, published in 1970.

When the computer retrieves data from the disk, via the disk interface, it must then forward it to the display and keyboard logic. In the illustrative embodiment of our invention, this is accomplished by providing a display interface (shown in detail in FIG. 3) between the disk interface and the display and keyboard logic. The display interface appears as a disk drive to the disk interface so that the disk interface can transmit data to it just as it does to a disk drive during a write operation. The display interface then re-transmits this data to the display and keyboard logic. The function of the display interface will be described in detail below in connection with FIG. 3.

Although the various signals transmitted between the blocks of FIG. 1 will be considered in detail below, it will be helpful at this point to briefly summarize the types of signals which are transmitted. Oscilloscope 20 can be a conventional oscilloscope such as Tektronix Model No. 604. The Tektronix Model No. 604 is described in detail in Tektronix Publication No. 070-1259-00 published in 1971 by Tektronix Incorporated. The horizontal sweep waveform appears on the X input of the oscilloscope, and vertical sweep waveforms appear on the +Y and −Y inputs. A positive signal on the +Y input and a negative signal on the −Y input both control an upward vertical deflection of the electron beam. Whenever the Z input is energized the electron beam strikes the screen and a point of light appears. When the Z input is low, the electron beam is cut off and the display is blanked. It is the display and keyboard logic which operates upon the data transmitted to it and derives the four signals for the oscilloscope.

The Keyboard

The eleven keys on keyboard 19 were described above. Keys P1-P8 transmit signals to the display and keyboard logic to identify one of eight patients. The reset (R) signal resets the circuitry in the display and keyboard logic, the cursor (C) signal is a command to move the cursor one position to the right in the display, and the display (D) signal is a command which indicates that a new ECG signal segment is to be displayed.

The DR11-A general purpose interface is provided with 16 input data lines IN 0-15 and 16 data output lines OUT 0-15. Whenever the computer, via the interface, has read a 16-bit word on the 16 input data lines, conductor DTR is pulsed to indicate that the data has been received. Similarly, whenever the computer has a 16-bit word to be transmitted over the data output lines, the data is accompanied by an NDR pulse. The REQA line, when pulsed, is a request for service by the peripheral equipment coupled to the interface (in this case, the display and keyboard logic); it is the pulsing of conductor REQA which generates the well-known "interrupt" signal.

Although 16-bit words can be transmitted from the computer, via the general purpose interface, to the display and keyboard logic, only three bits are required in the system of FIG. 1. It will be recalled that the continued operation of the display key by the physician causes successive ECG signal segments to be displayed. Even though the physician may have moved the cursor to a particular point along the horizontal time axis, if he continues to operate the display key segments recorded during succeeding minute intervals may be displayed. If this happens, the cursor must be moved on the display in order to inform the physician that he is now observing ECG signal segments in a different minute interval. Accordingly, when the computer determines that the cursor must be advanced — even though the physician has not advanced it and has simply continued to operate the display key — the computer forces bits 13, 14 and 15 in the 16-bit data output cable to the 1 state. When these three bits are all 1's, and the NDR conductor is pulsed, as will be described in detail below in connection with the display and keyboard logic, the cursor position is advanced to the right.

Also as will be described in detail below, in order to prepare the display and keyboard logic for the display of trend data for a new patient, an external initializing signal is required. This signal is transmitted by the computer over the same three data conductors (OUT 13, OUT 14 and OUT 15) by forcing all of them to the 0 state. The transmission of three 0's in this fashion, together with the NDR pulse, prepares the display and keyboard logic for the display of trend data for a new patient. Finally, in order to load the samples of a new ECG signal segment in the display and keyboard logic still another initializing signal is required. For this function a 110 code is transmitted, together with the NDR pulse.

The computer requires several different signals from the display and keyboard logic. The first is a signal informing the computer that the physician has operated the display key, that is, that a new ECG signal segment should be displayed. This signal is generated by pulsing the interrupt (REQA) conductor. The computer must also know the state of the display and keyboard logic, that is, what function it is performing at any particular time. As will be described below, the display and keyboard logic can assume four different states. The state of the logic circuit can thus be represented by two bits, and they appear on conductors IN 0 and IN 1 in the data input cable extended from the display and keyboard logic to the DR11-A general purpose interface. The computer must also be informed of the particular patient whose trend and ECG data is to be displayed. Since the physician can select any one of eight different patients, three bits are required to identify a selected patient, and the patient identification number is transmitted over the data input conductors IN 3, IN 4 and IN 5.

The computer must also know the position of the cursor on the display. While the physician may directly control movement of the cursor across the display by operating the cursor key, if the computer is not informed of a new cursor position it would not be able to transmit ECG signal samples taken at that time of day selected by the physician for review. Eight bits are required to represent the 256 positions of the cursor, and they are transmitted over data input lines IN 6 through IN 13 to the computer.

The last two lines between the DR11-A interface and the display and keyboard logic are conductors NDR and DTR. When any data word is to be transmitted from the computer, the NDR conductor is pulsed to inform the display and keyboard logic that a data word is present on the output lines. After the computer has read any input word, conductor DTR is pulsed to inform the display and keyboard logic that the word has been received.

The Disk Interface

The disk interface selects a particular one of several different disk drives with which it operates by pulsing a respective one of several DRIVE SEL conductors. As shown in FIG. 1, if the DRIVE SEL A conductor is pulsed, the RKO5 disk drive is selected. Depending on an address represented on several lines in cable 16, selected information is then read from a disk in that disk drive and transmitted through the disk interface to the computer. The data is transmitted over some of the other lines in cable 16. Most of the signals transmitted between the disk interface and a disk drive require low "assertion" levels, and it is for this reason that many of the signals in FIG. 1 are shown with a bar over them; in such a case, the "assertion" state is represented by the signal level on a respective conductor going low.

In order to select the display interface 17, the DRIVE SEL E conductor is energized by the disk interface. As far as the disk interface is concerned, display interface 17 appears to be another RKO5 disk drive. But it does not function as such a disk drive. Instead, it develops three signals — WRITE, WT CLK, and WT DATA(1) H — which are transmitted to the display and keyboard logic. The provision of the display interface is simply a convenient way to allow the same RK11-C disk interface which reads data from the basic ECG store (RKO5 disk drive) to transmit the data to the display and keyboard logic. Some kind of interface is needed because the RK11-C disk interface expects to "see" an RKO5 disk drive. But it is to be understood that the data could be retrieved from any other conventional type of memory, although at greater cost. (This is especially true if the computer is used for other purposes, such as monitoring the eight patients in the first place, analyzing their ECG signals and storing them on a disk, the equipments used for forwarding data to the display and keyboard logic therefore being available at no additional expense.)

The Display Interface

The operation of the display interface (FIG. 3) can be understood only with reference to the signals which the RK11-C disk interface transmits to an RKO5 disk drive and the signals which it expects to receive in return. Since in the system of our invention the disk interface communicates with the display interface only in the write mode, that is the only sequence which must be provided for.

At the start of a write operation (which, in this case, results in data being transmitted to the display and keyboard logic of FIGS. 4–11, rather than the writing of data on a disk), the RK11-C disk interface energizes the DRIVE SEL E conductor to select the display interface as opposed to the RKO5 disk drive which is also coupled to the disk interface. When this conductor goes low, inverter 23 on FIG. 3 energizes one input of each of AND gates 28 and 29. At the same time, the output of inverter 30 goes low to return assertion signals to the disk interface over the DRY, R/W/S RDY and HIDEN conductors. The disk interface expects to see assertion levels on these three conductors prior to taking the next step in the sequence.

An assertion level is then applied to the STROBE conductor. Since the DRIVE SEL E conductor is still low at this time, the outputs of both of inverters 22 and 23 are high and gate 24 operates. When the output of this gate goes high, 4-microsecond delay element 25 is triggered; at the end of the 4-microsecond delay period, one-shot multivibrator 26 is triggered. A two-microsecond negative pulse thus appears on the ADD ACK conductor 4 microseconds after the leading edge of the STROBE pulse, as expected by the disk interface.

At the trailing edge of the STROBE pulse, the output of gate 24 goes low, and one-shot multivibrator 27 is triggered. A ten-microsecond negative pulse appears on the SECTOR PULSE conductor, as expected by the disk interface.

Approximately 85 microseconds after the receipt of the pulse on this latter conductor, the disk interface causes the WRITE GATE conductor to go low. The output of inverter 31 goes high to energize one input of each of gates 28 and 29. Since the output of inverter 23 is still high at this time, gate 29 is energized to apply a positive potential on the WRITE conductor. This conductor is extended to the display and keyboard logic as will be described below, and it is energized prior to the transmission of data to the display and keyboard logic.

Two of the conductors on FIG. 1 are shown in dashed lines — conductors CLK LE H and WT DATA(1) H. These conductors are shown differently because the respective signals are taken from the back plane of the RK11-C disk interface; the assertion level in these two cases is high. The data bits themselves appear on the WT DATA(1) H conductor, and this conductor is extended directly through the display interface to the display and keyboard logic. Each data bit is accompanied by a clock pulse on conductor CLK LE H. Each clock pulse, applied to the third input of gate 28, causes the output of the gate to go high. The clock pulses thus appear on conductor WT CLK which is also extended to the display and keyboard logic.

Whenever the disk interface transmits data to a disk drive, 4,096 data bits are transmitted (corresponding to all of the data which can be stored on a single sector of a disk, as will be described below). Thus when data is to be transmitted to the display and keyboard logic, the WRITE conductor first goes high; while it remains high, 4,096 clock pulses appear on conductor WT CLK, with the accompanying potentials on conductor WT DATA(1) H representing bit values of 0 and 1. At the end of the transmission, the WRITE GATE and the DRIVE SEL E conductors go high in potential, the three conductors extended to the display and keyboard logic go low, and the data bit transmission sequence is terminated.

Display And Keyboard Logic (FIGS. 4–11)

Figure 4:
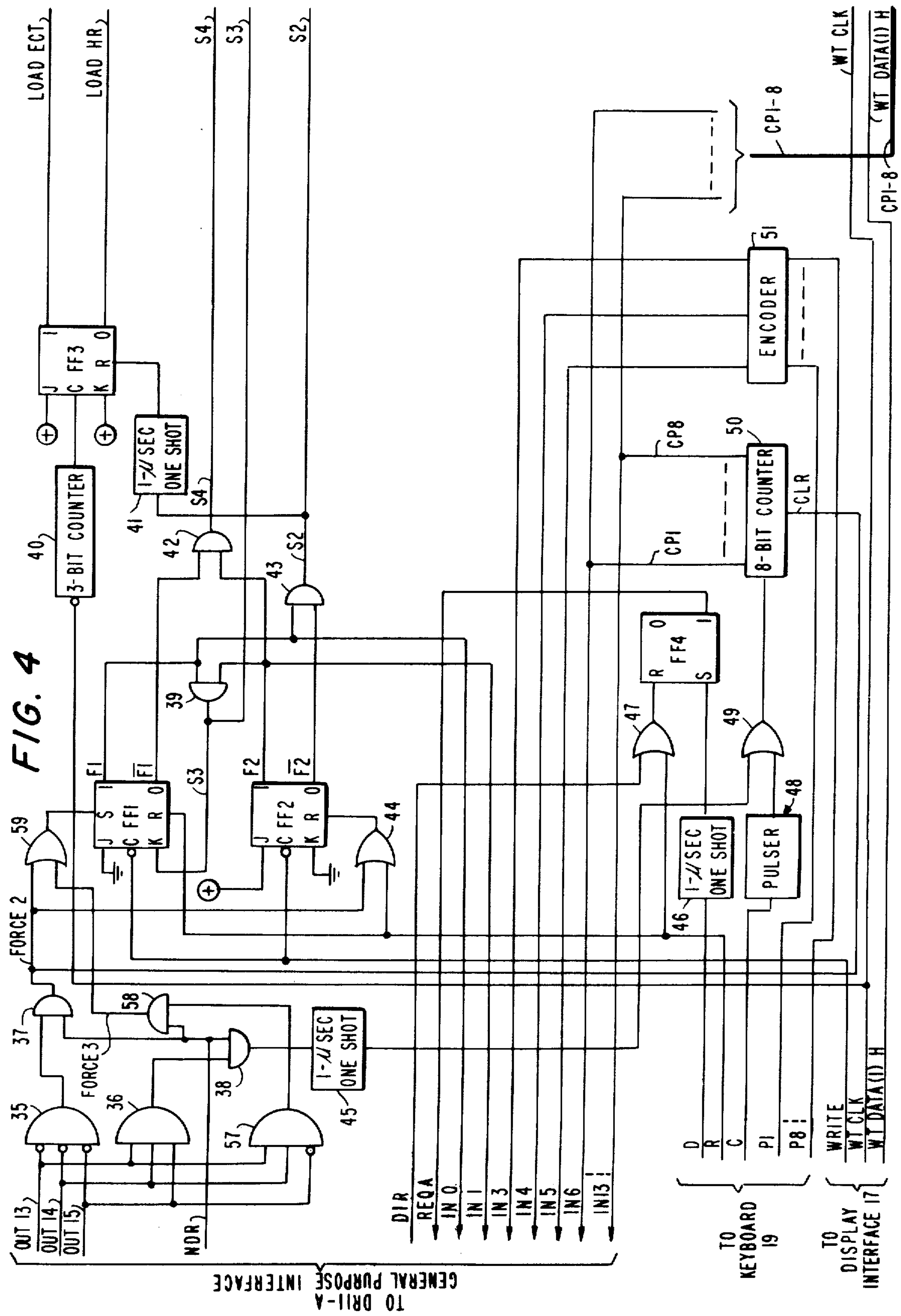
FIGS. 4–11 depict the circuitry included in the "display and keyboard logic" block of FIG. 1, with FIG. 4A depicting in detail the pulser block 48 of FIG. 4.

At the left of FIG. 4, there are shown all of the conductors which go from the display and keyboard logic to the display interface, the keyboard, and the DR11-A general purpose interface. (The four conductors — +Y, −Y, X and Z — extended to oscilloscope 20 are shown on FIG. 8.) One of conductors P1-P8 is energized depending upon which of the eight patient keys in keyboard 19 has been operated by the physician. These eight conductors are extended to the inputs of encoder 51, and the encoder functions to energize its three outputs to provide a 3-bit indication of the patient number. These three bits appear on conductors IN 3, IN 4 and IN 5 which are extended to the general purpose interface. Whenever the 16-bit data word from the display and keyboard logic is read by the computer, there are always three bits in the word which indicate the patient whose data is to be operated upon.

When the bounce-free cursor (C) key is operated, conductor C on FIG. 4 goes high. Referring to FIG. 4A, it will be noted that when conductor C first goes high, one-shot multivibrator 299 generates a pulse which is extended through OR gate 306 to OR gate 49 on FIG. 4. The count input of 8-bit counter 50 is pulsed to advance the count (the count can be incremented from 0 to 255). If the physician simply wants to move the cursor by one position to the right (corresponding to a 1-minute change), he releases the cursor key immediately after it is operated; only a single pulse is transmitted through OR gate 306, under control of one-shot multivibrator 199.

But if it is desired to advance the cursor a much greater distance, the cursor key is held down. The positive potential on conductor C (FIG. 4A) charges capacitor 301 through resistor 300. The capacitor is connected to the plus input of comparator 302, and a positive potential 303 is connected to the minus input of the comparator. Initially, the potential at the minus input is greater than the potential at the plus input. The output of the comparator is low and gate 305 remains unoperated. However, after the cursor key has been held down for ½-second, the potential across capacitor 301 exceeds the potential of source 303. As soon as the output of the comparator goes high, one input of gate 305 is energized. The other gate input is connected to the 25-Hz oscillator 304. Consequently, once the cursor key has been held down for ½-second, additional pulses are extended through OR gae 306 to OR gate 49 (FIG. 4). By holding the cursor key down, rather than simply closing it only momentarily, the cursor can be advanced at the rate of 25 positions per second.

Each pulse transmitted through OR gate 49 increments the count in counter 50. The 8-bit count appears on conductors CP1-CP8. These conductors are extended over cable CP1-8 to the circuitry which actually controls the display of the cursor. Thus it is the actual count in counter 50 that controls the cursor position, and this is under direct control of the physician. In order that the computer be able to determine the actual position of the cursor on the display, conductors CP1-CP8 are coupled to respective conductors IN 6 through IN 13 extended to the DR11-A general purpose interface. Whenever the 16-bit data word from the display and keyboard logic is read, the present position of the cursor is then made available.

When the bounce-free display (D) key is operated by the physician, one-shot multivibrator 46 is triggered. A 1-microsecond pulse is applied to the set input of flip-flop FF4 to set it in the 1 state. At this time conductor REQA goes high to request an interrupt. It is when the display key is operated by the physician that the computer is actually called on to provide data to the display and keyboard logic.

The reason for providing one-shot multivibrator 46 is that when the display key is operated by the physician, flip-flop FF4 is immediately set in the 1 state to generate the interrupt request pulse on conductor REQA. The computer typically recognizes the interrupt request, reads the data input word from the display and keyboard logic, and then pulses the DTR conductor even before the physician has released the display key. Since the DTR pulse must reset flip-flop FF4 it is necessary to insure that the display key, if it is still operated, does not prevent the flip-flip from resetting. Because multivibrator 46 is triggered only when the display key is first operated, and its output pulse is only 1-microsecond in width, by the time the DTR pulse arrives to reset flip-flop FF4, the set input is no longer energized. In order to generate another interrupt request, that and to control the display of a new ECG signal segment, the physician must release the display key and then operate it once again to cause flip-flop FF4 to switch from the 0 state to the 1 state.

When the computer services an interrupt request, in addition to being informed of the patient number involved and the cursor position on the display, the computer must know the state of the display and keyboard logic. Operations in the display and keybord logic are controlled by the combined states of flip-flops FF1 and FF2 on FIG. 4, and the sequencing of these flip-flops will be described below. The F1 output of flip-flop FF1 is coupled to data input conductor IN 0 ;and F2 output of flip-flop FF2 is coupled to the IN 1 data input conductor. Depending on the bit values of these two conductors, the computer can determine the state of the display and keyboard logic in order to take the appropriate action.

Thus, of the sixteen conductors in the data input cable extended from the display and keyboard logic to the DR11-A general purpose interface, two of them are used to represent the state of the display and keyboard logic, three of them are used to identify the patient of interest, and eight of them are used to represent the cursor position on the display. The other three conductors are not used.

Of the sixteen conductors in the data out cable extended from the DR11-A general purpose interface to the display and keyboard logic, only three of them are used. The three conductors OUT 13, OUT 14 and OUT 15 are forced by the computer to represent one of three codes. When all three conductors are forced to the 0 state, gate 35 is energized. Whenever a data word is transmitted over the data out cable, the general purpose interface energizes conductor NDR. Consequently, gate 37 operates to energize the FORCE 2 conductor whenever a 000 code is received. The FORCE 2 pulse is applied through OR gate 59 to the set input of flip-flop FF1, through OR gate 44 of the reset input of flip-flop FF2, and to the clear input of counter 50. As will be described below, when flip-flops FF1 and FF2 are set in the respective 1 and 0 states, the display and keyboard logic enters state S2.

When the three received data bits represent a 111 code, gate 36 operates. The output of this gate together with the NDR pulse operate gate 38 to trigger one-shot multivibrator 45. The one-microsecond pulse which is generated is transmitted through OR gate 49 to the input of counter 50. It will be recalled that it is necessary for the computer to control the advance of the cursor on the display when the ECG signal segment which is displayed occurred in a new one-minute interval. It is the triggering of one-shot multivibrator 45 which advances the cursor on the display under control of the computer, just as it is the triggering of one-shot multivibrator 48 which controls the advance of the cursor under the control of the physician.

When the received code is 011, gate 57 operates. Together with the NDR pulse, this causes gate 58 to operate and to energize the FORCE 3 conductor for transmitting a pulse through OR gate 59 to the set input of flip-flop FF1. As will be described below, this forces the display and keyboard logic to assume state S3.

It will be recalled that it is the setting of flip-flop FF4 in the 1 state that generates an interrupt request. But once an interrupt request has been recognized, the flip-flop must be reset; otherwise another interrupt request generated by the operation of the display key by the physician would not be recognized as distinct from the previous request. Since the DR11-A general purpose interface pulses the DTR conductor whenever an input word is read, the DTR pulse is extended through OR gate 47 to reset the flip-flop in the 0 state. Also, when the system is first turned on, it is desirable to reset the flip-flop. After the system is first turned on, the physician operates the reset (R) key in order to initialize the display and keyboard logic. The positive pulse on the R conductor is extended through OR gate 47 to reset flip-flop FF4. The same positive pulse is extended directly to the reset input of flip-flop FF1 and through OR gate 44 to the reset input of flip-flop FF2. This is to insure that both flip-flops are initially reset to define the first system state (idle) when the system is first turned on.

The System States

FIG. 13 depicts the four states S1-S4 of the system in terms of the states of flip-flops FF1 and FF2. In state S1, the system is idle, that is, it is not set up to receive any data from the display interface nor to control the display of any data. When he system is in state S2, trend data is loaded into various shift registers as will be described below. The trend data is used to form the ectopic beat and heartbeat rate displays. When the system is in state S3, the data representative of an ECG signal segment and an associated message are loaded in respective shift registers. Finally, when the system is in state S4, the previously loaded data is used to form the various displays.

When the system is first turned on, it is the operation of the reset key by the physician which initially sets both of flip-flops FF1 and FF2 in the 0 state to define the system idle state S1. It is the computer, by appropriately forcing the three data out conductors OUT 13, OUT 14 and OUT 15 to the 0 state, that causes the energization of the FORCE 2 conductor and the switching of flip-flop FF1 to the 1 state and the switching of flip-flop FF2 to the 0 state if it is not there already. Since conductor F2 is high when flip-flop FF2 is in the 0 state, and conductor F1 is similarly high when flip-flop FF1 is in the 1 state, gate 43 operates to energize conductor S2. It is a high potential level on this conductor that controls the trend loading operations to be described below. After the computer forces the system to state S2, it transmits 4,096 data bits through the disk interface and the display interface to the display and keyboard logic. As described above, at the start of a sequence the WRITF conductor, shown at the bottom left side of FIG. 4, goes high. Although this conductor is connected to the clock input of each of flip-flops FF1 and FF2, these flip-flops can be switched only by negative steps at their clock inputs. Consequently, when the WRITE conductor goes high it has no effect on these two-flops. During the "WRITE" operation, 4,096 clock pulses appear on conductor WT CLK, together with 4,096 data bit values on conductor WT DATA(1) H.

It should be noted that prior to the loading of the trend data for a new patient, when the FORCE2 conductor first goes high counter 50 is cleared. This is done to control return of the cursor to the left side of the screen prior to review of the ECG data for the new patient.

Following the loading of the 4,096 trend data bits in the system, in a manner to be described below, the WRITE conductor goes low. A negative step thus appears at the clock input of each flip-flops FF1 and FF2. Since the J input of flip-flop FF1 is permanently ground, and conductor S3 connected to the K input of the same flip-flop is also low (since gate 39 is not energized when the system is in state S2), the negative clock pulse applied to the clock input of flip-flip FF1 has no effect on its state. However, since the J input of flip-flop FF2 is connected to a positive potential and its K input is grounded, the negative clock pulse causes this flip-flop to be set in the 1 state. Both flip-flops are now in the 1 state to define system state S3 as shown on FIG. 13. Both of conductors F1 and F2 are high so that gate 39 is energized, to in turn cause conductor S3 to go high. It is while the system is in state S3 that another 4,096 data bits are transmitted to be loaded into respective shift registers for controlling the display of both an ECG signal segment and an associated message.

Figure 3:
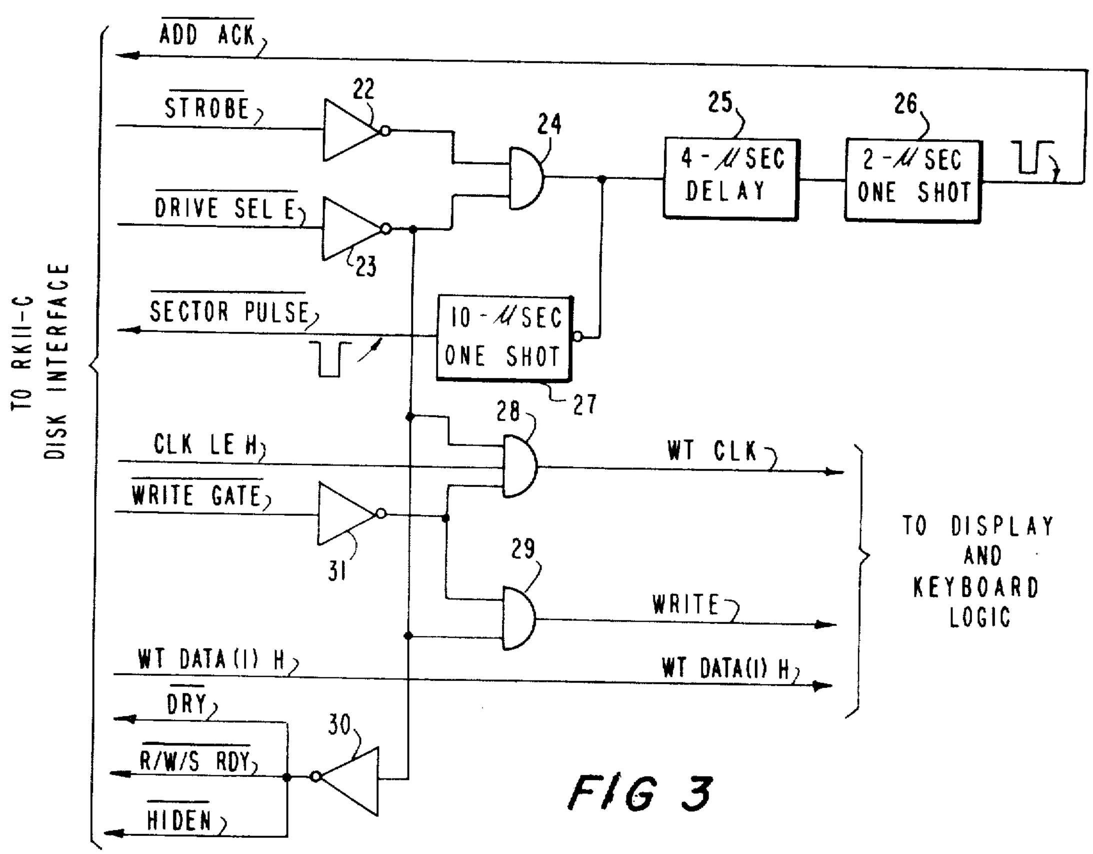
FIG. 3 depicts the circuitry within the "display interface" block of FIG. 1.

Once again, during the transmission of these 4,096 data bits, the WRITE conductor is high, under control of the display interface of FIG. 3. At the termination of the transmission sequence, the WRITE conductor goes low. This has no effect on flip-flop FF2 since the only thing it could control is the setting of the flip-flop in the 1 state and it is already there. However, since the K input of flip-flop FF1 is now high as a rsult of the energization of conductor S3, the clock pulse applied to flip-flop FF1 causes it to switch to the 0 state. The output of gate 39 now goes low. Because conductor F1 and conductor F2 are both high, gate 42 is energized to cause conductor S4 to go high. As will be described below, when this conductor is high a display is formed on the oscilloscope. The system remains in state S4 so that a continuous display can be seen.

In the absence of the operation of a key by the physician, the system remains in state S4. Whenever the display key is operated, the computer forces the system to state S3 so that new ECG waveform and message data can be loaded. However, as will be described below, if a new patient identification number appears on conductor IN3, IN4 and IN5, the computer forces the system to state S2 to that new trend data can be loaded prior to the loading of new waveform and message data.

Packing of Trend Data

In the illustrative embodiment of the invention, each heartbeat and ectopic beat rate value comprises eight bits (to define one of 256 levels). But the trend data for each patient is actually stored in an intermeshed fashion. The first eight-bit byte in the 4,096 bits of trend data comprises the first heartbeat rate value, the second eight-bit byte comprises the first ectopic beat rate value, the third eight-bit byte comprises the second heartbeat rate value, the fourth byte comprises the second ectopic beat rate value, etc. Alternate eight-bit bytes must be directed to two different shift registers, as will be described in connection with FIG. 5, in order that all of the trend data of each of the two types is loaded in a respective shift register. Flip-flop FF3 on FIG. 4 is used to control the loading of alternate eight-bit bytes of data in the two different shift registers.

When the system is first placed in state S2 and conductor S2 goes high, one-shot multivibrator 41 is triggered. The one-microsecond pulse which is thus generated resets flip-flop FF3 in the 0 state. The LOAD HR conductor goes high to control the loading of the first byte in the respective heartbeat rate shift register. The positive clock pulses appear on conductor WT CLD applied to the input of three-bit counter 40. The counter is incremented at the trailing edge of each pulse. After eight pulses have been counted, a positive "carry" pulse is applied to the clock input of flip-flop FF3. This causes the state of the flip-flop to switch; at this time, the LOAD HR conductor goes low, and the LOAD ECT conductor goes high to control the loading of the next eight-bit byte in the respective ectopic beat shift register. Following the counting of another eight bits (while an ectopic beat rate value is being stored in the respective shift register), the carry pulse at the output of counter 40 once again switches the state of flip-flop FF3 so that the LOAD HR conductor gos high once again rather than the LOAD ECT conductor. It is apparent that counter 40 and flip-flop FF3 control the alternate storage of eight-bit bytes in respective shift registers in order that each register may contain only the respective type of trend data.

CRT Refresh Memory

Figure 5:
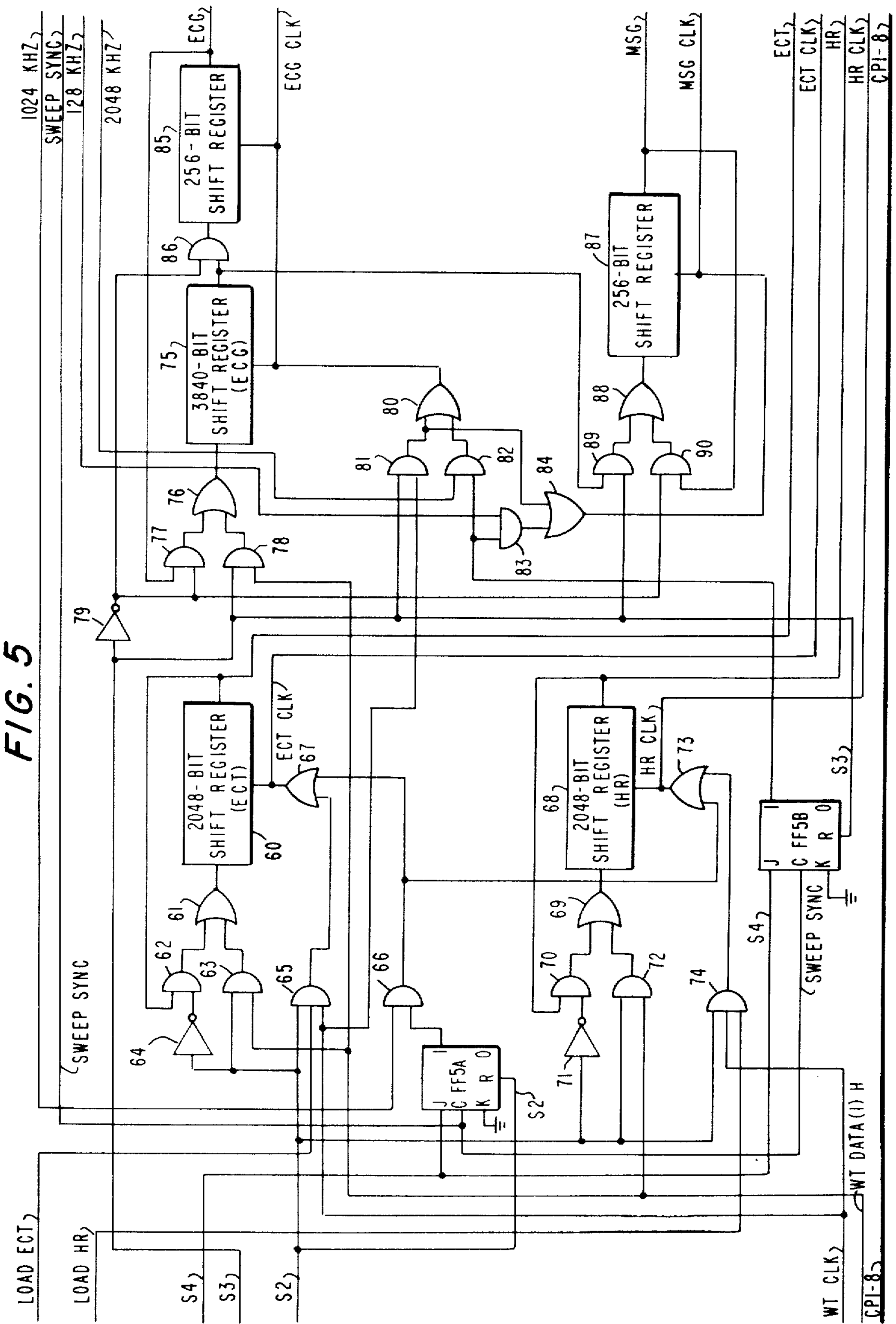

Shift registers 60 and 68 on FIG. 5 are the two shift registers for storing the heartbeat rate and the ectopic beat rate trend values. As described above, when the system is first plced in state S2, the LOAD HR conductor is high and the LOAD ECT conductor is low. With the former conductor high, one input of gate 74 is enabled. The input of this gate connected to conductor S2 is similarly high. The clock pulses which appear on conductor WT CLK are applied to the third input of gate 74, and consequently the clock pulses are transmitted through this gate and through OR gate 73 to the clock input of 2048-bit shift register 68, the shift register which is used to store the heartbeat rate trend values. The data input bits on conductor WT DATA(1) H are applied to one input of gate 72, the other input of which is connected to conductor S2. Thus the data bits are transmitted through gate 72, and through OR gate 69 to the data input of shift register 68. A clock pulse is applied to the clock input for both 0 and 1 data bits, while the data input is energized only for a 1 data bit. As is well known in the art, this results in the storage of successive data bits in the shift register and their shifting to the right. It should be noted that gate 70 is not energized at this time because with conductor S2 high, the output of inverter 71 is low. The first eight-bit byte (the first heartbeat rate value) is thus stored in shift register 68 during the first eight clock pulses in the trend loading sequence. Although data bits are transmitted through gate 63, because gate 65 is disabled and clock pulses are not applied to the clock input of register 60, no bits are stored in this register.

After the first eight data bits are stored in this manner, conductor LOAD HR goes low, and it is now conductor LOAD ECT which goes high. Gate 74 is thus disabled, while gate 65 is enabled. The three inputs to gate 65 are conductors S2, WT CLK and LOAD ECT. Consequently, clock pulses are now transmitted through gate 65 and OR gate 67 to the clock input of shift register 60, rather than through gate 74 and OR gate 73 to the clock input of shift register 68. Both of gates 63 and 72 are enabled by the S2 signal, and consequently the data bits on conductor WT DATA(1) H are transmitted through both gates and through respective OR gates 61 and 69 to the respective data inputs of the two shift registers. However, data is loaded only into shift register 60 because it is only this shift register which has its clock input pulsed by gate 65 (through OR gate 67). After eight data bits have been stored in this shift register, flip-flop FF3 on FIG. 4 changes state once again, so that the next eight-bit byte is stored in shift register 68 rather than shift register 60.

This process continues with alternate eight-bit bytes in the stream of 4,096 trend data bits being stored in alternate shift registers, until eventually 2,048 bits (256 8-bit values) have been stored in each shift register and both of the WT CLK and WT DATA(1) H conductors go low at the end of the data transmission sequence.

ECG Data Loading

As soon as the trend data is loaded in this manner, the system switches to state S3 as described above in connection with FIG. 4. Conductor S2 goes low in potential. At this time, the output of each of inverters 64 and 71 goes high in order to enable one input of each of gates 62 and 70. Each bit shifted out of register 60 appears at the other input of gate 62, and each bit shifted out of register 68 appears at the other input of gate 70. Consequently, gates 62 and 70 serve to control the recirculation of the bits in the respective shift registers when the respective shift register clock pulses (HR CLK and ECT CLK) are derived from the output of gate 66 through respective OR gates 67 and 73. However, gate 66 has one of its inputs connected to the 1 output of flip-flop FF5A, and this flip-flop is initially reset by the positive potential on conductor S2 during the trend loading sequence. Consequently, recirculation does not begin immediately after trend data is loaded into the shift registers. The trend data simply remains stationary in these shift registers (all registers on FIG. 5 are of the "static" type, that is, they do not require refresh pulses), until recirculation of the data is required as will be described below.

It should also be noted that recirculation of each shift register data is to be prevented whenever new trend data is being loaded, that is, whenever conductor S2 is high. Since this conductor is connected to the reset input of flip-flop FF5A, the flip-flop is reset prior to the loading of new data and recirculation of the trend data is inhibited.

It is when the system is in state S3 that 4,096 bits are loaded into shift registers 75 and 87, these 4,096 bits representing both an ECG signal segment and the associated message. The 4,096 bits which are transmitted consist of a 256-bit message, followed by 480 8-bit ECG data samples. During the ECG (and message) data loading, no bits are stored in 256-bit shift register 85. Instead, the bits enter shift register 75 and are then shifted out of this register into shift register 87. After 4,096 data bits have been received, the first 256 bits reside in register 87, while the last 3,840 bits reside in shift register 75.

The ECG data sample loading is accomplished when the system is in state S3 and conductor S3 is high. The output of inverter 79 is low to disable gate 86, so that no bits are shifted into shift register 85. Similarly, gates 77 and 90 — both of which control the recirculation of shift register bits — are disabled. The three gates which are enabled by a high potential on conductor S3 are gates 78, 81 and 89. Gate 78 has its other input connected to conductor WT DATA(1) H, on which the data bits appear. Consequently, the data bits are transmitted through gate 78 and OR gate 76 to the input of shift register 75 and are stored in this register as a result of clock pulses appearing at the clock input. The clock pulses are derived through OR gate 80, and more specifically that input of the gate which is connected to the output of gate 81. One input of this latter gate is enabled by conductor S3, and the other input is connected to conductor WT CLK on which there appear the clock pulses which accompany the data bits. The clock pulses which appear at the output of gate 81 are also extended through OR gate 84 to the clock input of shift register 87 so that the first 256 bits in the 4,096-bit sequence which are shifted out of register 75 can be transmitted through gate 89 and OR gate 88 for storage in register 87. After 4,096 bits have been transmitted in this manner, shift register 87 contains the 256-bit message which is to be displayed above the ECG signal segment, and register 75 contains the 3,840 bits which define the waveform to be displayed.

Recirculation & Display

After the loading of the ECG sample data, conductor S3 goes low and the output of inverter 79 goes high. At this time, recirculation gates 77 and 90 are both enabled. When recirculation of the shift register data is to occur, the 1 output of flip-flop FF5B is high to enable gates 82 and 83. The clock pulses for controlling the recirculation of the data in shift register 87 are applied to the other input of gate 83 at a 128-kHz rate (the reason for the various clock rates will be explained below), and they are transmitted through OR gate 84 to the clock input of the shift register. Data bits shifted out of the register are transmitted through gate 90 and OR gate 88 back to the input of the shift register. Similarly, gate 82 is enabled because one of its inputs is connected to the 1 output of flip-flop FF5B. The other input to this gate has applied to it clock pulses at a 2,048-kHz rate for causing the recirculation of bits in registers 75 and 85. The clock pulses are transmitted through gate 82 and OR gate 80 to the clock inputs of both of shift registers 75 and 85. When the system is in state S4 (the state during which recirculation occurs), gate 89 is disabled and gate 86 is enabled. Consequently, bits shifted out of register 75 are transmitted through gate 86 and stored in shift register 85; bits shifted out of register 85 are recirculated through gate 77 and OR gate 76 back to the input of shift register 75.

Shift register 85 initially contains 256 0's. (Clock pulses applied to the clock input of the register during state S3, when gate 86 is held off, clear the register.) It is the bits on conductor ECG at the output of shift register 85 that actually control the display of the ECG signal segment. Because the first 256 bits are always 0's, the first ¼-second portion of the waveform display s blanked, as shown on FIG. 2. It is only after 256 0's have been shifted out of the register that the 3,840 bits initially in shift register 75 can control the display of non-zero values. The reason for providing shift register 85 is that in order to control proper synchronization of the system, 4,096 ECG sample data bits must be recirculated in the time that it takes for one complete horizontal sweep on the display to take place. Thus shift register 85 functions as an artificial delay and is required solely for synchronization purposes.

Figures 14, 15:
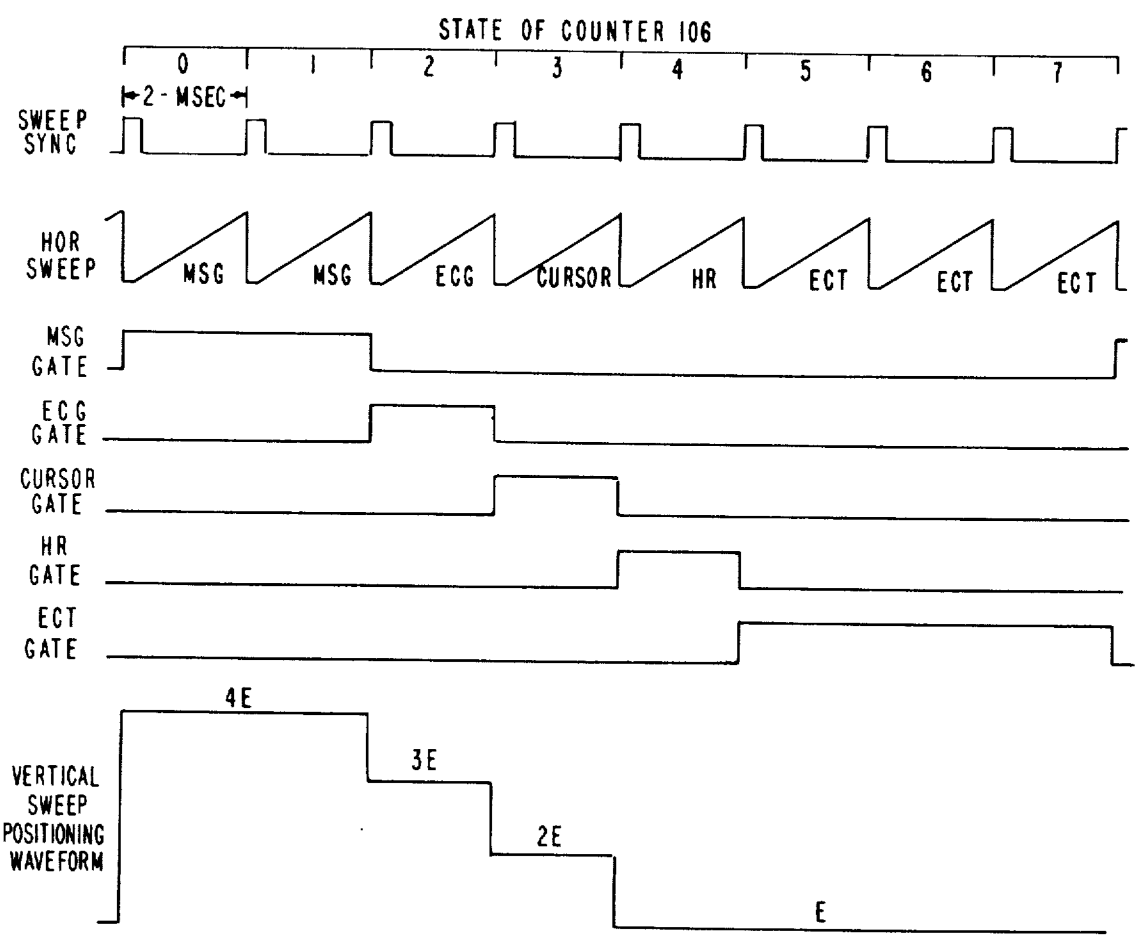
FIG. 14 depicts several waveforms which will be helpful in understanding the operation of the display and keyboard logic and, in particular, the circuitry on FIG. 10.
FIG. 15 is a table which will aid in understanding the several clock rates which are required for the different types of displays.

When data is stored in the various shift registers on FIG. 5, it is stored at a rate determined by the clock pulse rate on the WT CLK conductor. However, when the data bits are to be recirculated, different clock rates are required for the various shift registers. Each horizontal sweep of the display requires two milliseconds and for proper synchronization the complete recirculation of bits in any shift register (shift registers 75 and 85 are considered as s single shift register for recirculation purposes) must occur within two milliseconds. FIG. 15 will be helpful in understanding the different clock rates. The message shift register 87, which contains the 256 bits which comprise the message to be displayed, requires a recirculation clock rate of 128 kHz in order that 256 bits be completely recirculated in two milliseconds. It is for this reason that 128-kHz clock pulses, which appear on the similarly labeled conductor, are applied to one input of gate 83, since it is this gate which controls the recirculation of the data bits in shift register 87 when the system is in state S4.

The 4,096 bits in serially connected shift registers 75 and 85 require a shifting rate of 2,048 kHz in order that a complete recirculation occur in two milliseconds. For this reason, it is the 2,048-kHz conductor connected to an input of gate 82 which is used to control recirculation of the data samples.

Each of registers 60 and 68 which contains 2,048 trend bits requires a clock rate of 1,024 kHz in order that a complete recirculation occur in two milliseconds. Consequently, the clock input to gate 66 which controls the recirculation is connected to the 1,024-kHz conductor. Finally, as shown on FIG. 15, in order to display the cursor, a 128-kHz clock is required, but this will be described below in connection with the development of the cursor signal.

For the proper functioning of the system, the recirculation of the bits in the various shift registers must be synchronized with the horizontal sweeps across the face of the display. At the end of each horizontal sweep, a short positive pulse appears on the SWEEP SYNC conductor, as will be described below. It will be recalled that initially flip-flop FF5A is reset while the trend data is being loaded during state S2. Consequently, gate 66 which controls the transmission of recirculating clock pulses to the shift registers 60 and 68 is disabled. But as soon as the system enters state S4, the J input of flip-flop FF5A goes high. The flip-flop remains in the 0 state, however, since its state does not change until its clock input goes high. but as soon as the first SWEEP SYNC pulse is generated, the leading edge triggers the clock input of the flip-flop and it switches to the 1 state. At this time, gate 66 is enabled to control recirculation of the bits in shift registers 60 and 68 in synchronism with the next horizontal sweep.

Gates 82 and 83 control the recirculation of the bits in shift registers 75, 85 and 87. These gates can transmit respective clock pulses only when flip-flop FF5B is in the 1 state. This flip-flop is initially reset when conductor S3 goes high, that is, preparatory to the loading of new ECG and message data bits in the shift registers. After the loading, the system switches to state S4 as described above and the J input of flip-flop FF5B goes high. However, the flip-flop does not switch to the 1 state to initiate the recirculation of bits until the SWEEP SYNC pulse is received. It is only when the flip-flop is triggered by the leading edge of the SWEEP SYNC pulse that the flip-flop switches to the 1 state so that the recirculation of the bits in shift registers 75, 85 and 87 can begin in synchronism with a horizontal sweep.

Reloading ECG Data

It should be noted that new trend data is loaded into registers 60 and 68 only when the physician is interested in retrieving data for a new patient. Otherwise, if all that he wants to observe is a new ECG waveform for the same patient, it is only the data in registers 75, 85 and 97 which must be changed. Consequently, flip-flop FF5A is reset by the positive potential which appears on conductor S2 only when new trend data is being loaded, and it is switched to the 1 state when the system enters state S4 and the now-loaded data is to be displayed. But flip-flop FF5B is reset by a positive potential on conductor S3, that is, when new ECG data is being loaded in registers 75, 85 and 87. While such data is being loaded, since flip-flop FF5A is still in the 1 state, the data in registers 60 and 68 continues to recirculate. Following the loading, as soon as the system switches to state S4, flip-flop FF5B switches to the 1 state and the ECG and message data begins to recirculate as well in order to properly form the various displays.

The 4-Channel Display

Figure 6:
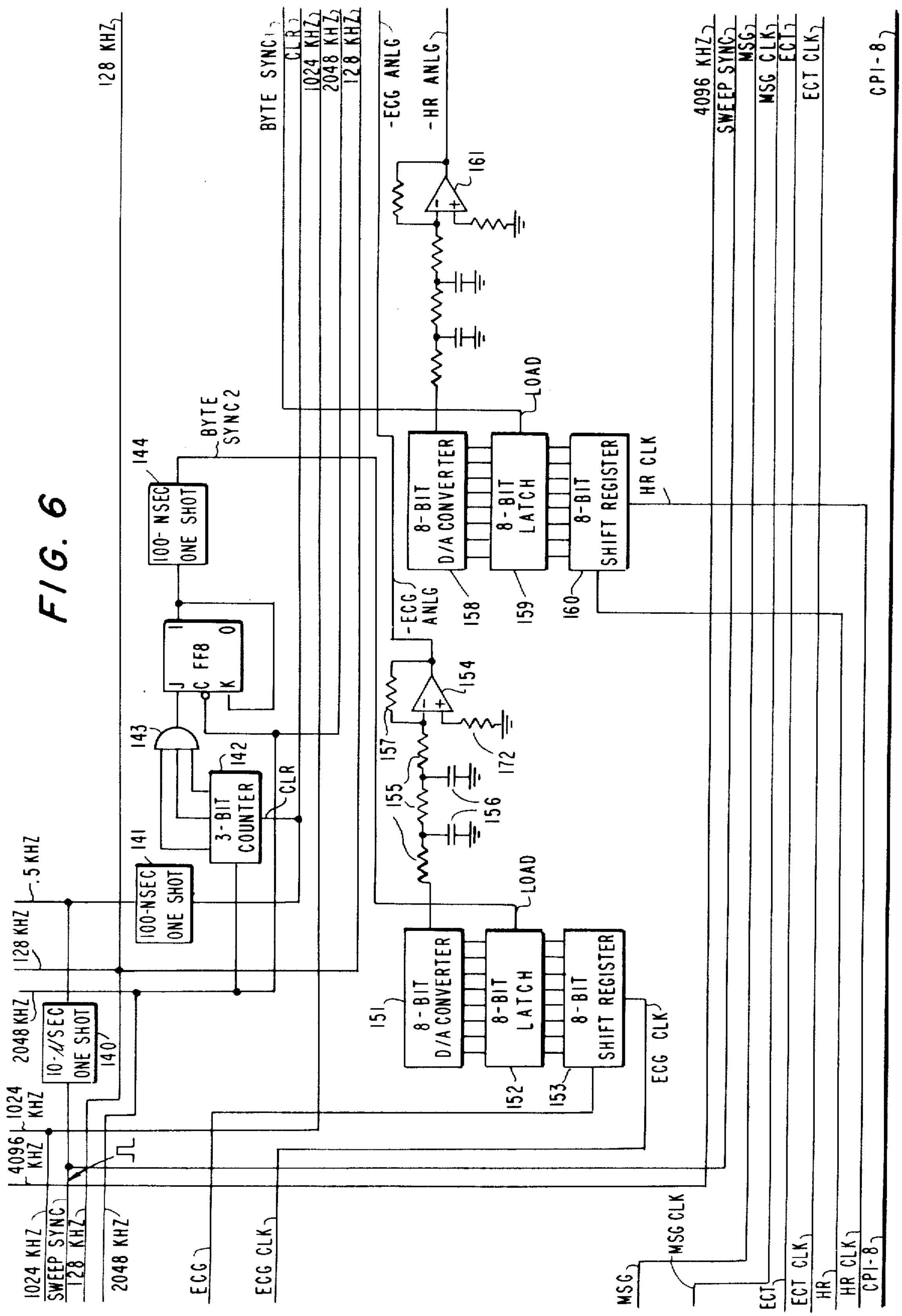

In addition to the cursor position data on cable CP1-8, eight conductors are extended from FIG. 5 to FIG. 6. When the system is in state S4, data bits appear continuously on the four conductors, ECG, MSG, ECT and HR. The data bits are used to form four different displays. Each of these four data conductors has an associated clock conductor on which there appear clock pulses in synchronism with the respective data bits. In each 2-millisecond interval, 4,096 bits appear on the ECG conductor (together with 4,096 clock pulses on the ECG CLK conductor) in order to control the display of an ECG signal segment as will be described below. In the same interval, 256 bits appear on the MSG conductor (together with 256 clock pulses on the MSG CLK conductor) in order to control the display of the associated message. Similarly, in every two milliseconds, 2,048 bits appear on each of the ECG and HR conductors, together with the same number of clock pulses on the respective clock conductors, in order to control the display of the two types of trend data. All four data bit sequences are synchronized with the horizontal sweeps, that is, the first bit in each sequence appears on the respective data conductor immediately following the leading edge of the SWEEP SYNC pulse.

FIG. 14 depicts the basic horizontal sweep timing of the display. A complete display is formed in 16 milliseconds. Each horizontal sweep requires two milliseconds, and consequently there are eight horizontal sweeps in each frame. The eight sweeps are identified by the count of three-bit counter 106 on FIG. 10 which will be described below. At the start of each 2-millisecond interval, a SWEEP SYNC pulse is generated.

The pulse is ten microseconds in duration and one of the functions of the SWEEP SYNC pulse is to synchronize the recirculating data on FIG. 5, as described above.

a. CRT Sweep Waveforms

FIG. 14 shows the eight SWEEP SYNC pulses which occur in each 16-millisecond frame. During each of the first two horizontal sweeps, the message at the top of the display is formed. The message is written twice during each 16-millisecond frame to achieve improved brightness. During the third horizontal sweep, the ECG waveform is developed directly below the message. During the fourth sweep, the cursor is developed on the face of the oscilloscope, and during the fifth sweep the heartbeat rate plot is formed. Finally, during each of the last three horizontal sweeps, the ectopic beat rate histogram is developed, three sweeps being used for the purpose of improved brightness.

Five different gating signals are developed to control the five different types of displays. The MSG GATE signal is high for the first two horizontal sweeps during each 16-millisecond frame to enable the circuitry which controls the display of the message. The ECG GATE is high for only two milliseconds in each 16-millisecond cycle to enable the circuitry which forms the ECG waveform display. Similar remarks apply to the CURSOR GATE and HR GATE waveforms. Finally, the ECG GATE pulse is 6-milliseconds wide in order to enable the circuitry which forms three superimposed ectopic beat rate histogram displays.

The displays are formed by causing each of the five different types of horizontal sweeps to be positioned at a different vertical level on the face of the display. Thus the vertical sweep positioning waveform, as shown in FIG. 14, is repetitive at 16-millisecond intervals. During the first two horizontal sweeps of each 16-millisecond cycle, the vertical sweep positioning waveform is at its highest level of 4E. This controls the positioning of the message at the top of the screen. The 4E level is a "bias" level in that it is the base level for the vertical deflecting voltage during a horizontal sweep across the screen. The message is actually formed by rapidly modulating the vertical deflecting voltage on the 4E base line. To develop the ECG waveform on the display, the vertical sweep positioning waveform is held at a level of 3E for two milliseconds, and it is then held at a level of 2E for two milliseconds in order to form the cursor. This causes the cursor to be displayed below the ECG waveform. Finally, during the last half of each 16-millisecond cycle, the vertical sweep positioning waveform is held at level E in order to form the two rate (trend) plots. As will be described below, when the heartbeat rate (HR) plot is developed, the modulating signal for the vertical deflecting voltage is boosted so that the heartbeat rate plot is formed above the ectopic beat rate histogram.

With respect to FIG. 14 it should be noted that the SWEEP SYNC pulses are shown exaggerated in width; each pulse is only ten-microseconds wide — only a fraction of each two-millisecond horizontal sweep. As will be described below, the oscilloscope is blanked whenever a SWEEP SYNC pulse is generated. It will be recalled that it is the leading edge of each SWEEP SYNC pulse which initiates the recirculation of bits in the shift registers of FIG. 5. Consequently, the initial portion of each display on the oscilloscope may be blanked, but this is of no moment; it simply means that a very small portion of the information which could be displayed is not.

b. System Clock

Figure 9:
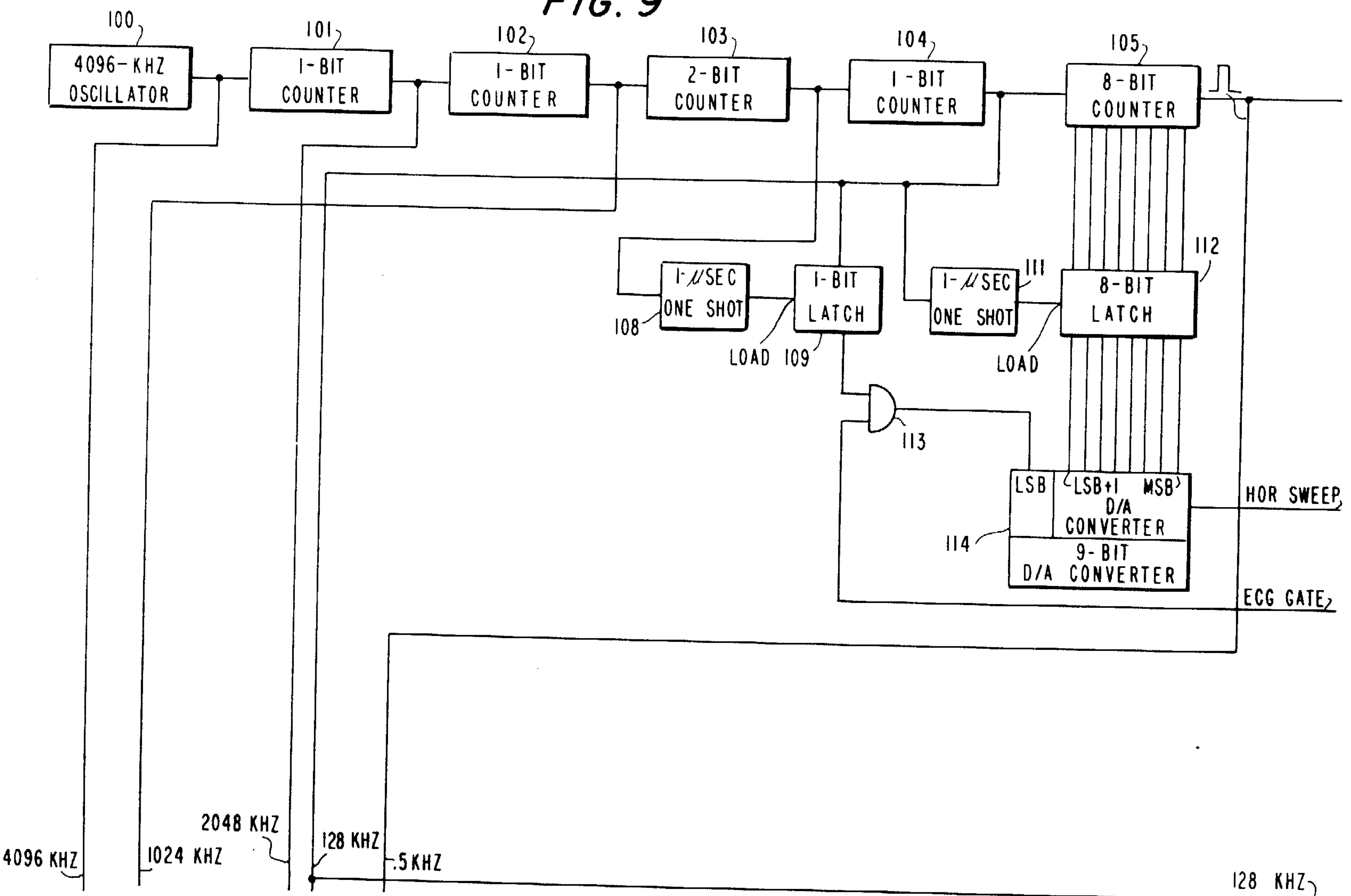

FIG. 9 depicts the clock generating circuits of the system. The basic clock used in the system is 4096-kHz oscillator 100. Counters 101–105 are all triggered when negative steps are applied to their inputs. The first counter 101 generates a 2048-kHz clock waveform and counter 102 generates a 1024-kHz clock waveform. The 2-bit counter 103 functions to divide the clock pulses of counter 102 by a factor of 4, and consequently a 256-kHz clock waveform appears at its output. Since counter 104 is a divide-by-two circuit, at its output there appears a 128-kHz clock waveform. Finally, the 8-bit counter 105 provides pulses at its output at the rate of 0.5 kHz. This is equivalent to a two-millisecond clock cycle, and it is each pulse at the output of counter 105 which is used to derive the SWEEP SYNC pulse as will be described below in connection with FIG. 6.

c. Analog Display Generation

Except for the ECG waveform display, each display is considered to have 256 positions in the horizontal direction. That is, display information must be provided for each of 256 positions when each horizontal sweep is in progress. The 256 positions along each horizontal sweep are represented by the state of 8-bit counter 105. The count represented by the counter is converted to an analog voltage which drives the horizontal sweep of the oscilloscope. Consequently, the continuing incrementing of the count in the counter results in a staircase horizontal sweep voltage.

The eight bits contained in counter 105 are extended to the eight inputs of 8-bit latch 112. Each time that the count in the counter changes, it is stored in the latch. Since the count in the counter changes on the negative edge of each pulse at the output of counter 104, it is desirable to use the positive edge of each pulse at the output of counter 104 to strobe the latch.. This insures that the outputs of counter 105 settle down prior to the strobing of the latch. Thus it is each positive step at the output of counter 104 which triggers one-shot multivibrator 111. When triggered, this multivibrator generates a 1 -microsecond pulse which energizes the LOAD input of latch 112 to store in it the count of the counter.

d. Sequencing of Horizontal Sweeps

The eight bits stored in latch 112 are extended to the eight most significant bits of digital-to-analog converter 114. The output of this converter is a staircase horizontal sweep waveform of the conventional type used to control the horizontal sweep of an oscilloscope. The HOR SWEEP conductor at the output of digital-to-analog converter 114 is extended to the horizontal sweep of the oscilloscope used to form the display. It should be noted that counter 105 cycles from zero through 255 in two milliseconds since the carry pulses generated at its output occur at a 0.5-kHz rate; each staircase thus occupies 2 milliseconds, less the flyback time of under 10 microseconds.

The eight bits stored in latch 112 are applied to the eight most significant bits of converter 114. The converter is actually a 9-bit device but for all horizontal sweeps except the ECG waveform sweep only the eight most significant positions of the converter are used; for all horizontal sweeps except that used to develop the ECG waveform only 256 horizontal positions (defined by 8 bits) must be taken into account.

However, when an ECG waveform is developed, 512 positions along the horizontal sweep are accounted for since shift registers 75 and 85 on FIG. 5 contain 512 8-bit bytes. Accordingly, when the horizontal sweep is developed during the third sweep of each 16-millisecond cycle (see FIG. 14), the least significant bit position of the 9-bit digitial-to-analog converter is also supplied with bit information. The output of counter 104 is extended to the input of latch 109. The LOAD input of the latch is triggered by one-shot multivibrator 108 just as the LOAD input of latch 112 is triggered by one-shot multivibrator 111. It is the positive step at the output of counter 103 which triggers multivibrator 108 in order that latch 109 be set after the output of counter 104 has settled.

The ECG GATE conductor is high in potential during the two milliseconds when the ECG waveform is being formed on the display. Consequently, gate 113 is enabled during only these two milliseconds of each 16-millisecond cycle. When the gate is enabled, it extends 0 and 1 level potentials to the least significant bit input of the digital-to-analog converter at a 256-kHz rate (the rate at which clock pulses are generated at the output of counter 103). This means that the output of the converter consists of 512 steps, rather than 256 steps, with each step in the 512-step waveform having half the magnitude of a step in the staircase sweep voltage developed during the other four types of horizontal sweeps.

The steps in the horizontal sweep staircase should be developed on a one-to-one basis with the separate samples displayed during the course of any horizontal sweep. Three of the waveform displays require 256 samples each. (Although the message has only 32 characters in it, each character is formed by an 8-column vertical raster, there thus being 256 samples required for the 32-character message.) The additional resolution for the ECG waveform is derived by using the least significant bit of the 9-bit digital-to-analog converter. The least significant bit is held at the 0 level in the absence of the energization of the ECG GATE conductor.

Referring to FIG. 14, it will be recalled that five GATE signals must be developed to control the eight sweeps during each 16-millisecond cycle. These GATE waveforms are developed by the circuitry on FIG. 10. The 0.5-kHz clock waveform at the output of counter 105 is extended to the input of 3-bit synchronous counter 106 on FIG. 10. This counter cycles to energize output conductors B1, B2 and B4 in a binary counting mode. Inverters 114 are used to derive the three complementary signals B1, B2 and B4. Gates 117–121 are used to derive three of the GATE signals directly, and in conjunction with the flip-flops FF6 and FF7 to derive the other two.

When the counter represents a count of 000, the three inputs of gate 121 are energized, the gate output goes high, and flip-flop FF6 is set in the 1 state. Referring to FIG. 14, it will be noted that at the start of each 16-millisecond cycle, the MSG GATE waveform should go high, and the ECT GATE waveform (which was high previously) should go low. When flip-flop FF6 is set in the 1 state, its 1 output goes high to generate the MSG GATE pulse. Similarly, the reset input of flip-flop FF7 is energized to cause this flip-flop to be reset and the ECG GATE conductor to go low. Since each of the other four gates 117–120 has at least one of its inputs low at this time, none of them is energized.

When counter 106 represents a count of 001 (i.e., B1=1, B2=0 and B4=0), following the first 2-millisecond horizontal sweep in each 16-millisecond cycle, gate 121 turns off but this has no effect on the two flip-flops whose states remain unchanged. Nor does any of the other four gates have all three of its inputs energized; consequently, no changes occur in the two flip-flop states, nor in the five GATE waveforms. Referring to FIG. 14, it will be noted that this is the desired operation since the MSG GATE waveform must remain high for two horizontal sweeps.

When the count in counter 106 advances to 010, of the five gates, only gate 120 is energized. Consequently, the ECG GATE waveform goes high. At the same time the reset input of flip-flop FF6 is energized to reset this flip-flop in the 0 state so that the MSG GATE conductor goes low in potential, as required with reference to FIG. 14.

When the count advances to 011, only gate 119 operates to generate the CURSOR GATE positive pulse. The ECG GATE conductor goes low at this time with the turning off of gate 120.

At a count of 100, gate 118 turns on to energize the HR GATE conductor. At the same time, gate 119 turns off so that the CURSOR GATE conductor goes low in potential.

Finally, when the counter advances to 101, gate 117 operates to set flip-flop FF7 in the 1 state. This causes the ECT GATE conductor to go high, as required by the timing waveforms on FIG. 14, at the same time that the HR GATE conductor goes low. Even though the count is then advanced to 110, and then to 111, none of gates 117–121 operates. It is only when the count recycles to 000 that gate 121 operates once again to set flip-flop FF6 in the 1 state and to reset flip-flop FF7 in the 0 state, so that the ECT gate conductor can go low and the MSG GATE conductor can go high.

e. Vertical Sweeps

The five gate waveforms are used directly to develop the vertical sweep positioning waveform shown on FIG. 14. Operational amplifier 123 is arranged in a conventional configuration with its plus input connected through a resistor of magnitude R/2 to ground and with its output being coupled back to its minus input through a resistor of magnitude R. The minus input of the operational amplifier is connection through four respective resistors of magnitudes R, R/2, R/3 and R/4 to four different conductors, on each of which there is the same level potential when it is high. Both the HR GATE and ECT GATE conductors are connected to inputs of OR gate 122, and consequently this gate operates whenever either of these two conductors is high in potential. When this happens, the output of operational amplifier 123 is negative and it has a magnitude E. Since the MSG GATE conductor is extended to the minus input of the operational amplifier through a resistor of magnitude R/4, when the MSG GATE conductor is high the output of the operational amplifier is at level −4E. Similarly, when the CURSOR GATE and ECG GATE conductors are high, the respective levels at the output of the operational amplifier 123 are −2E and −3E. Since only one of the four inputs to the minus terminal of the operational amplifier is energized at any one time, it is apparent that the vertical sweep positioning waveform is that shown in FIG. 14, except that it is a negative step waveform, labeled -STAIRCASE in FIG. 10. Since the -STAIRCASE signal, after being combined with two other signals to be described below, is applied to the −Y input of the oscilloscope, the overall effect is that of a positive deflecting voltage — for controlling upward deflection of the electron beam in the oscilloscope.

The Digital to Analog Conversion

FIG. 6 includes the circuitry for converting the recirculating ECG waveform samples and the heartbeat rate trend samples to analog forms. It will be recalled that at the start of each horizontal sweep, the output of counter 105 (FIG. 9) goes high, pulses appearing at the output of the counter at a 0.5-kHz rate. These pulses are extended to the input of one-shot multivibrator 140 on FIG. 6, to control generation of the 10-microsecond SWEEP SYNC pulses as shown. The positive pulse on the 0.5-kHz conductor occurs in synchronism with the first bit on each of the ECG and HR conductors on FIG. 6, these bits being derived from respective shift registers 85 and 68 on FIG. 5.

The pulses on the ECG conductor are applied to the input of 8-bit shift register 153, and the synchronized timing pulses on conductor ECG CLK are applied to the clock input of the shift register. Consequently, eight successive bits are stored in the shift register, each 8-bit byte corresponding to one sample of the ECG waveform to be developed on the display. After an entire 8-bit sample is stored in the register, the load input of 8-bit latch 152 is pulsed so that the 8-bit sample can be retained in the latch while a new sample is being stored in the shift register. Since the ECG data bits occur at a 2048-kHz rate (see FIG. 15), it is apparent that the LOAD input of latch 152 must be pulsed at a rate of 256-kHz. Elements 141–144 and flip-flop FF8 are used to derive the LOAD pulses for latch 152.

Figure 16:
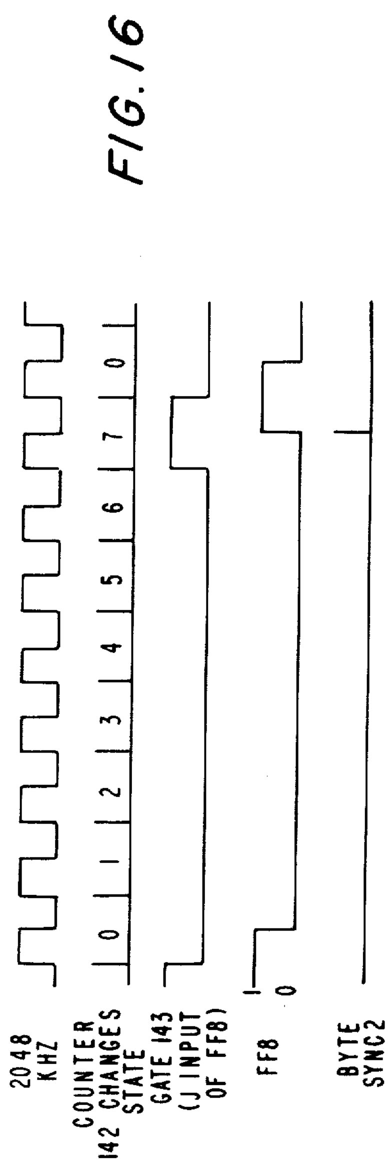
FIG. 16 depicts timing waveforms which will aid in understanding the operation of the display and keyboard logic and, in particular, the circuitry on FIG. 6.

At the start of each horizontal sweep, the positive edge of the pulse at the output of counter 105 triggers one-shot multivibrator 141. The positive edge of the resulting 100-nanosecond pulse on conductor CLR clears 3-bit counter 142. The 2048-kHz clock pulses are applied to the count input of the counter, and its three outputs are connected to the inputs of gate 143. Consequently, after a count of 111 has been reached, the output of gate 143 goes high to enable the J input of flip-flop FF8. FIG. 16 depicts the 2048-kHz clock pulses, together with the manner in which counter 142 changes state. The counter changes state at the positive edge of each clock pulse, and the count in the counter cycles between 0 and 7 as shown.

Assume that initially flip-flop FF8 is in the 0 state. Its 1 output is therefore low; since the 1 output is fed back to the K input of the flip-flop, the K input is similarly low. Before a count of 111 is reached, the J input of the flip-flop is also low. With both inputs low, the clock pulses applied to the C input of the flip-flop have no effect; the flip-flop remains in the 0 state. But as soon as a count of 111 is reached, gate 143 is energized and its output goes high for one cycle of the 2048-kHz clock as shown in FIG. 16. Thus for this clock cycle the J input of the flip-flop is high. At the trailing edge of the 2048-kHz clock pulse which advanced counter 142 to a count of 111 in the first place, the negative step at the C input of flip-flop FF8 causes the flip-flop to switch state as shown in FIG. 16. The 1 output of the flip-flop goes high to enable the K input. As soon as the count in the counter switches from 111 to 000, the J input goes low as shown in FIG. 16. Consequently, the trailing edge of the clock pulse which recycled the count back to 000 causes the flip-flop to switch back to the 0 state since its J input is low and its K input is high. The cycle then repeats itself.

Whenever the 1 output of the flip-flop goes high, one-shot multivibrator 144 is triggered. The resulting 100-nanosecond pulse on the BYTE SYNC2 conductor causes latch 152 to be loaded with the contents of shift register 153. Since it requires eight clock pulses at a 2048-kHz rate until multivibrator 144 is triggered, it is apparent that the BYTE SYNC2 pulses occur at a 256-kHz rate, that is, immediately after each 8-bit byte is stored in shift register 153.

The eight outputs of latch 152 are extended to 8-bit digital-to-analog converter 151 which develops an analog voltage whose magnitude is proportional to the value of the digital sample contained in latch 152. The output of the converter is passed through a low-pass filter comprising resistors 155 and capacitors 156 to remove switching transients, and it is then applied to the minus input of operational amplifier 154, whose plus input is grounded through resistor 172 and which is provided with a feedback resistor 157. The resulting negative signal at the output of the operational amplifier, labeled −ECG ANLG in the drawing, is a negative signal whose magnitude at any instant corresponds to the respective digital sample contained in latch 152.

Eight-bit samples of heartbeat rate values appear on the HR conductor, together with synchronized clock pulses on conductor HR CLK. Referring to FIG. 15, it will be recalled that these data bits occur at a 1024-kHz rate, two milliseconds thus being required for all 2,048 bits in shift register 68 (FIG. 5) to be shifted out when the system is in state S4 so that 256 sample values can be displayed to form the heartbeat rate trend plot. Each 8-bit byte which is stored in shift register 160 is transferred to a 8-bit latch 159 when the respective LOAD conductor is pulsed. The sample in the latch is applied to the eight inputs of digital-to-analog converter 158 which develops an analog voltage whose magnitude is proportional to the sample value stored in latch 159. The analog output of the converter is passed through a low-pass filter and then buffered by operational amplifier 161 to develop the −HR ANLG signal in a manner comparable to that in which the −ECG ANLG signal is developed. The major difference between the development of the two signals is that latch 159 must have its LOAD input pulsed at a rate which is different from the rate at which latch 152 is operated. That is because the data bits on the HR conductor occur at a 1024-kHz rate rather than a 2048-kHz rate.

Figure 7:
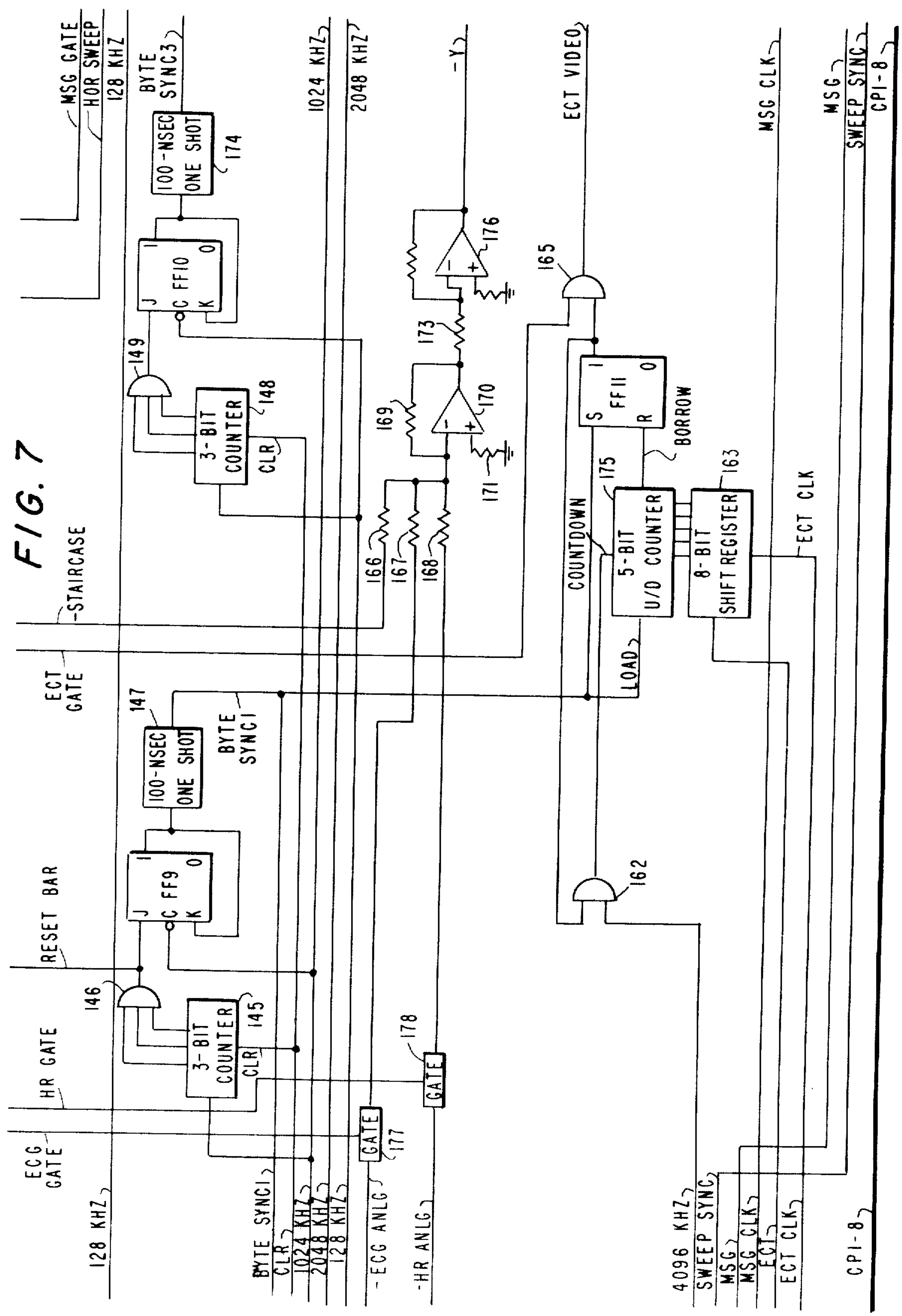

It will be recalled that elements 141–144 and flip-flop FF8 are used to derive the BYTE SYNC2 pulses at a 256-kHz rate. Elements 145-147 and flip-flop FF9 on FIG. 7 are used to derive the BYTE SYNC1 pulses at a 128-kHz rate in the same manner. The output of multivibrator 141 (FIG. 6) clears counter 145, and then the BYTE SYNC1 pulse is developed via waveforms which are essentially comparable to those shown in FIG. 16. The only difference between the two sub-systems is that the clock input of flip-flop FF9 and the count input of counter 145 are connected to the 1024-kHz conductor whereas the clock input of flip-flop FF8 and the count input of counter 142 are connected to the 2048-kHz conductor. Consequently, the BYTE SYNC1 pulses are generated at half the rate of the BYTE SYNC2 pulses. This is to be expected since to develop the ECG waveform display 512 8-bit samples are accounted for during each horizontal sweep, whereas to ›rm the heartbeat rate trend plot only 256 8-bit samles are required for each horizontal sweep.

The output of gate 146 is connected to the RESET ·AR conductor, and the function of the pulse on this onductor when gate 146 is operated will be explained elow.

Figure 10:
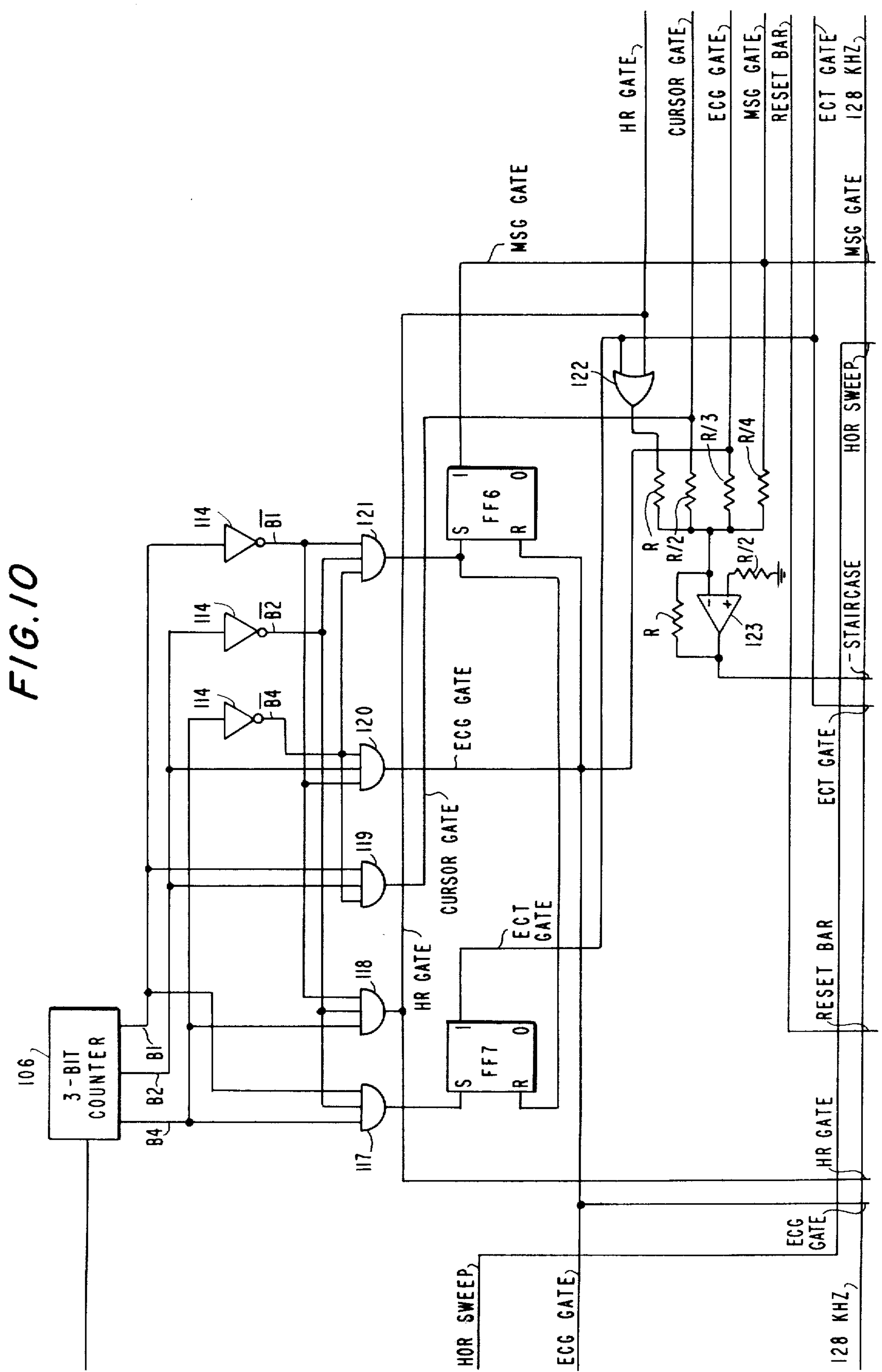

The −STAIRCASE waveform (see FIG. 14 — the ertical sweep positioning waveform), developed by ıe circuitry on FIG. 10, is extended through summing esistor 166 to the minus input of operational amplifier 70 on FIG. 7. The =ECG ANLG and −HR ANLG ignals are similarly extended through respective anaog gates 177 and 178, and respective summing resisors 167 and 168 to the minus input of the same operaional amplifier. The operational amplifier thus oper.tes as an adder, since its plus input is grounded hrough resistor 171 and it is provided with a feedback esistor 169. Each analog gate is operated only when its espective control input, ECG GATE or HR GATE, is ıigh. When an analog gate is operated it passes a re.pective analog signal through it with no distortion. During each horizontal sweep when an ECG waveform s to be formed, the negative analog signal which repreıents the ECG waveform is added to positioning level −3E of the vertical deflecting waveform, and during each sweep when a heartbeat rate plot is to be formed, he respective negative analog trend signal is adding to positioning level −E of the vertical deflecting waveform. Thus during the formation of each of the two continuous waveforms on the display, the vertical deflecting voltage is modulated in accordance with the data to be displayed, and the base level of the vertical deflecting voltage is held fixed at a value which properly positions the respective display on the screen. Because operational amplifier 170 inverts the signals applied at its minus input, its output is positive. However, this positive signal is extended through resistor 173 to the minus input of operational amplifier 176 which functions as another inverter. The resulting signal is negative and it is applied to the −Y input of the oscilloscope to control a positive deflection of the electron beam. During those horizontal sweeps when messages, cursors and ectopic beat trend plots are formed, analog gates 177 and 178 remain off. Thus the −Y deflecting voltage is not modulated and simply controls the base level of the horizontal sweep. The necessary vertical modulating signals are applied to the +Y input of the oscilloscope, as will be described below.

Each ectopic beat rate sample value consists of eight bits. The data bits and the respective clock pulses appear on conductors ECT and ECT CLK at a rate of 1024 kHz (see FIG. 15). This is the same rate at which data bits and clock pulses appear on the HR and HR CLK conductors. Consequently, the pulses on the BYTE SYNC1 conductor can be used to identify complete ectopic beat rate value samples just as these pulses are used to identify complete heartbeat rate value samples. The data bits on conductor ECT are applied to the input of 8-bit shift register 163 on FIG. 7 and the respective clock pulses on conductor ECT CLK are applied to the clock input of the shift register. Although each sample comprises eight bits, the maximum ectopic beeat rate sample value which is considered is 32. (More than 32 ectopic beats per minute is highly unlikely). Accordingly, only the five least significant bits in shift register 163 are used to derive each vertical bar in the ectopic beat rate histogram. The five least significant bits in shift register 163 are loaded into 5-bit up/down counter 175 each time that its LOAD input is pulsed, that is, with the generation of each BYTE SYNC1 pulse.

The technique for forming each vertical bar in the display is to first convert the digital sample in counter 173 to a pulse whose duration is proportional to the sample magnitude. This is accomplished by having gate 162 pulse the "countdown" input of counter 175, each pulsing of this input causing the count of the counter to be decremented until a BORROW pulse is generated at its output after the count has been decremented to 00000.

Samples are loaded into the counter at a 128-kHz rate (the BYTE SYNC1 rate). This means that there are slightly more then eight microseconds — while a new sample is being loaded in shift register 163 — to fully decrement the counter from a maximum count of 11111 to the final count of 00000. Since counting up to 32 in slightly more than eight microseconds can be accomplished with a 4096-kHz clock, it is the 4 96-kHz clock which is used to decrement the counter. The 4096-kHz conductor is connected to one input of gate 162. The other input to the gate is connected to the 1 input of flip-flop FF11 which is initially high, the flipflop being set in the 1 state by each BYTE SYNC1 pulse at the same time that a new sample is loaded into the counter. Consequently, clock pulses are continuously applied to the countdown input of counter 175. As soon as the count has been decremented to 00000, the resulting BORROW pulse at the output of the counter resets flip-flop FF11. The 1 output now goes low to disable gate 162 so that no further clock pulses are extended through the gate.

Although data bits appear on the ECG conductor during every 2-millisecond cycle and are continuously stored in register 163 and counter 175, it is only during those horizontal sweeps when the ectopic beat rate histogram is to be formed that gate 165 is enabled. This is achieved by coupling one input of the gate to the ECT GATE conductor. Each BYTE SYNC1 pulse which causes a sample to be loaded into counter 175 also sets flip-flop FF11 in the 1 state. As soon as this happens, the 1 output of the flip-flop enables gate 162 so that the count in counter 175 can be decremented. Furthermore, the 1 output of the flip-flop enables one input of gate 165. If the ECT GATE conductor is high, which it is during the horizontal sweeps when the histogram is being formed on the display, gate 165 energizes its output from the moment that a new sample is loaded into the counter (with the generation of the BYTE SYNC1 pulse) until the BORROW pulse is generated. Consequently, the output of gate 165, connected to the ECT VIDEO conductor, is a pulse whose width is proportional to the magnitude of a respective sample initially stored in counter 175.

The ECT VIDEO conductor is coupled to one input of OR gate 266, whose output is connected to an input of gate 268. The other input of gate 268 is connected to the output of inverter 267 whose input is coupled to the SWEEP SYNC conductor. Gate 268 functions to derive the Z input signal to the oscilloscope. When the output of the gate goes high, the electron beam is allowed to form an image on the screen. During each horizontal retrace, the beam should be blanked and it is for this reason that inverter 267 is provided; gate 268 can energize its output only when a horizontal sweep is in progress, and not during the retrace. Of the five inputs to OR gate 266, the only one which can be energized during a sweep used to develop the ectopic beat rate histogram is the ECT VIDEO conductor. Thus gate 268 energizes its output only for a time interval corresponding to the magnitude of the vertical bar which is to be displayed. The output of gate 268 is extended through emitter follower 269, resistor 270 and cable 271 to the Z input of the oscilloscope.

As will be described below with reference to FIG. 11, the histogram is actually developed by generating a 256-step raster which is applied to the vertical deflection plates of the oscilloscope via the +Y input. Thus were the Z axis not blanked at all, 256 vertical bars each of maximum height would appear at the bottom of the screen. However, because the Z axis is unblanked for only a variable initial portion of each raster sweep (see FIG. 2), each sweep causes a vertical bar to be "drawn" in the upward direction only for a length of time corresponding to the presence of the ECT VIDEO signal. It is in this way that the output of gate 165 controls the formation of the ectopic beat rate histogram.

The CRT Blanking

In addition to the ECT VIDEO input to OR gate 266, there are four other inputs. The HR GATE and ECG GATE inputs unblank the electron beam during complete respective horizontal sweeps in order to form the two respective continuous displays. The MSG VIDEO input is pulsed whenever a dot in a character must be formed, as will be described below. The BLIP input is pulsed for 40 microseconds during a sweep used to form the cursor; this, too, will be described below.

Figure 11:
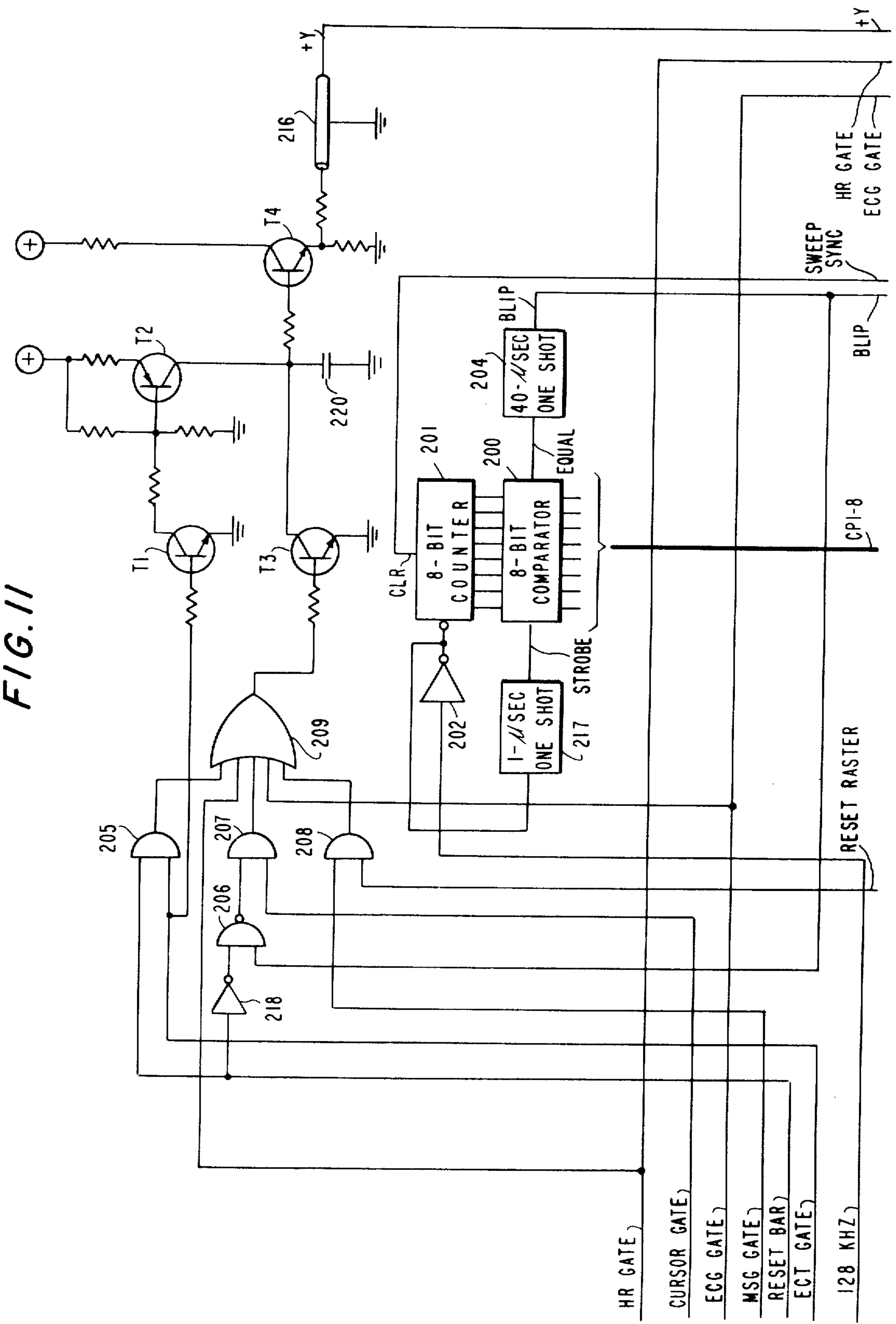

A vertical raster is developed by the circuit of FIG. 11 to control the display of the message, the cursor and the ectopic beat rate histogram. The size of the vertical raster is greater when the histogram is formed since the maximum height of a bar at the bottom of FIG. 2 is greater than the height of both the cursor and the characters in the message. On FIG. 11, transistors T1, T2, T3 and T4 form a conventional buffered sawtooth generator. Transistor T2 functions as a constant current source for charging capacitor 220 to produce a linear ramp voltage across it. Transistor T3 is a clamp which serves to discharge capacitor 220 rapidly when the transistor is turned on. Transistor T4 functions as an emitter follower to drive cable 216 which is coupled to the +Y input of the oscilloscope. Thus, the +Y input to the oscilloscope is a vertical raster which follows the sawtooth waveform which appears across capacitor 220. With transistor T1 held off the height of the vertical raster is that required for the display of the message and the cursor. In order to increase the height of the vertical raster when the histogram is being formed on the screen, the ECT GATE conductor is coupled to the base of transistor T1. During those horizontal sweeps when the histogram is being formed, transistor T1 turns on to lower the base voltage of transistor T2. This increases conduction in transistor T2 and thus capacitor 220 charges at a higher rate. This results in a larger height for the vertical raster.

In order to reset the ramp developed across capacitor 220, that is, to start a new sawtooth waveform, or to prevent sawtooth generation altogether, the output of OR gate 209 must go high. When the heartbeat rate plot is being formed, the vertical raster is not required at all. Consequently, the HR GATE conductor is connected to one input of OR gate 209 to prevent the application of the vertical raster signal to the +Y input of the oscilloscope during those horizontal sweeps when the heartbeat rate plot is being formed on the screen. Similarly, when the ECG waveform is being formed on the screen, the vertical raster should not appear on the +Y input of the oscilloscope. It is for this reason that the ECG GATE conductor is connected to a second input of OR gate 209 to inhibit the generation of the vertical raster.

The ECT GATE conductor is connected to one input of gate 205. Thus this gate is enabled during those horizontal sweeps when the histogram is being formed on the display. The other inputs to gate 205 is coupled to the RESET BAR conductor. Referring back to FIG. 7, it will be noted that this conductor is pulsed each time that the output of gate 146 goes high. This occurs when the count in counter 145 reaches 111 in preparation for the loading of a new ectopic beat rate sample value in counter 175. The RESET BAR conductor is thus pulsed at the end of the slightly more than eight microseconds alloted to the formation of each vertical bar in the histogram (assuming that the maximum time is required in order to form a bar of maximum height). Even though the ECT VIDEO conductor in most cases goes low prior to the end of this slightly more than eight-microsecond interval in order to blank the electron beam, the sawtooth waveform on the +Y conductor must be allowed to continue to increase to the maximum amplitude in order that a vertical bar in the histogram of maximum height be formed if it is required. But at the end of each cycle which is slightly in excess of eight microseconds, the RESET BAR conductor is pulsed so that gate 205 energizes the third input of OR gate 209. This causes capacitor 220 to discharge and a new ramp to begin to develop across the capacitor so that the next vertical bar in the histogram can be drawn.

The MSG GATE conductor is connected to one input of gate 207. Thus this gate is enabled during those horizontal sweeps when a message is being formed on the display. Each character in a message is developed by appropriately unblanking the Z input of the oscilloscope during each of several vertical sweeps for the character. But at the end of each sweep, capacitor 220 must be discharged so that another sweep can begin. As will be described in connection with FIG. 8, the RESET RASTER conductor goes high after each vertical line in a character has been developed and it does not go low once again until the start of the next line. Consequently, the RESET RASTER waveform can be used to discharge capacitor 220. The RESET RASTER conductor is connected to the second input of gate 208, and together with the MSG GATE waveform causes OR gate 209 to discharge capacitor 220 between raster sweeps during the formation of a message across the screen.

Finally, gate 207 energizes the fifth input of OR GATE 209 to discharge capacitor 220 and to keep it discharged when necessary during those horizontal sweeps when the cursor is being formed. It is during these 2-millisecond sweeps that the CURSOR GATE conductor, connected to one input of gate 207, is high. The other input to the gate is connected to the inverting output of gate 206. One input to gate 206 is connected to the RESET BAR conductor. This conductor goes high at a 128-kHz rate, and remains high only while counter 145 on FIG. 7 represents a count of 111. The other input to gate 206 is connected to the BLIP conductor, which, as will be described below, contains on it a 40-microsecond positive pulse during those aster sweeps when the cursor is actually formed. The iming of the pulse within the 2-millisecond horizontal weep period depends upon the position at which the ursor is to be formed. While the BLIP pulse appears, henever the RESET BAR conductor goes low within he 40-microsecond BLIP- pulse interval the output of ate 206 goes low. It is at this time that a vertical line s drawn as part of the cursor. As soon as the RESET AR conductor goes high, the output of gate 206 goes igh to control the discharge of capacitor 220. Consequently, the vertical lines which are drawn to form the ursor are drawn only when the count in counter 145 is ther than 111. The left edge of the cursor depends pon the leading edge of the pulse on the BLIP conductor, and the leading edge of this pulse is timed to coincide with the cursor position represented in counter 50 FIG. 4); thus it is the left edge of the cursor that actully represents a specific time along the horizontal axis of the display. The width of the cursor depends upon he width of the pulse on the BLIP conductor. Since the pulse is 40 microseconds wide, and RESET BAR pulses ccur at a 128-kHz rate, the cursor is actually formed y only several vertical lines on the display.

The pulse on the BLIP conductor is developed by the circuitry associated with counter 201 and comparator 200. The 8-bit cursor position count in counter 50 (FIG. 4) is extended over cable CP1-8 to 8-bit comparator 200. At the start of each horizontal sweep, the SWEEP SYNC pulse clears counter 201. As mentioned above in connection with FIG. 15, a 128-kHz clock is required to form the cursor. This is because there are 256 vertical line positions which must be taken into account when the cursor is formed, and since a horizontal sweep requires 2 milliseconds, the 256 positions along the horizontal axis of the display can be defined by a 128-kHz clock. Pulses on the 128-kHz conductor are applied to the input of inverter 202. Each time that the output of the inverter goes low, the count in 8-bit counter 201 is incremented. Each time that the output of inverter 202 goes high, one-shot multivibrator 217 is triggered. The resulting 1-microsecond output pulse from the multivibrator is used to STROBE comparator 200. It is during the 1-microsecond STROBE pulse that the comparator functions to see if the count in counter 201 matches the count in counter 50. It should be noted that the STROBE pulse is generated midway between successive incrementations of the counter, in order that the count settle by the time each comparison is made. Counter 201 cycles through 256 counts in 2 milliseconds as a result of the use of the 128-kHz clock. At some time during the 2-millisecond horizontal sweep the comparator energizes its EQUAL output to indicate that the count in the counter matches the count in counter 50. At this time one-shot multivibrator 204 is triggered to generate the 40-microsecond BLIP pulse described above. The leading edge of the pulse occurs at a time during each 2-millisecond horizontal sweep which depends upon the ratio of the count in counter 50 to the maximum count of 256.

The BYTE SYNC3 pulses are required for the message display. They are derived by counter 148, gate 149, flip-flop FF10 and one-shot multivibrator 174, all on FIG. 7. These elements derive the BYTE SYNC3 pulse just as elements 145-147 derive the BYTE SYNC1 pulse. The only difference is that the clock input of flip-flop FF10 and the count input of counter 148 are connected to the 128-kHz conductor, rather than to the 1024-kHZ conductor. This is because during the formation of the message, 32 characters are formed within 2 milliseconds. The BYTE SYNC3 pulses occur at a 16-kHz rate so that there are 32 such pulses during each horizontal sweep, each pulse initiating the formation of a different character.

THE DETAILED MESSAGE GENERATION

Figure 8:
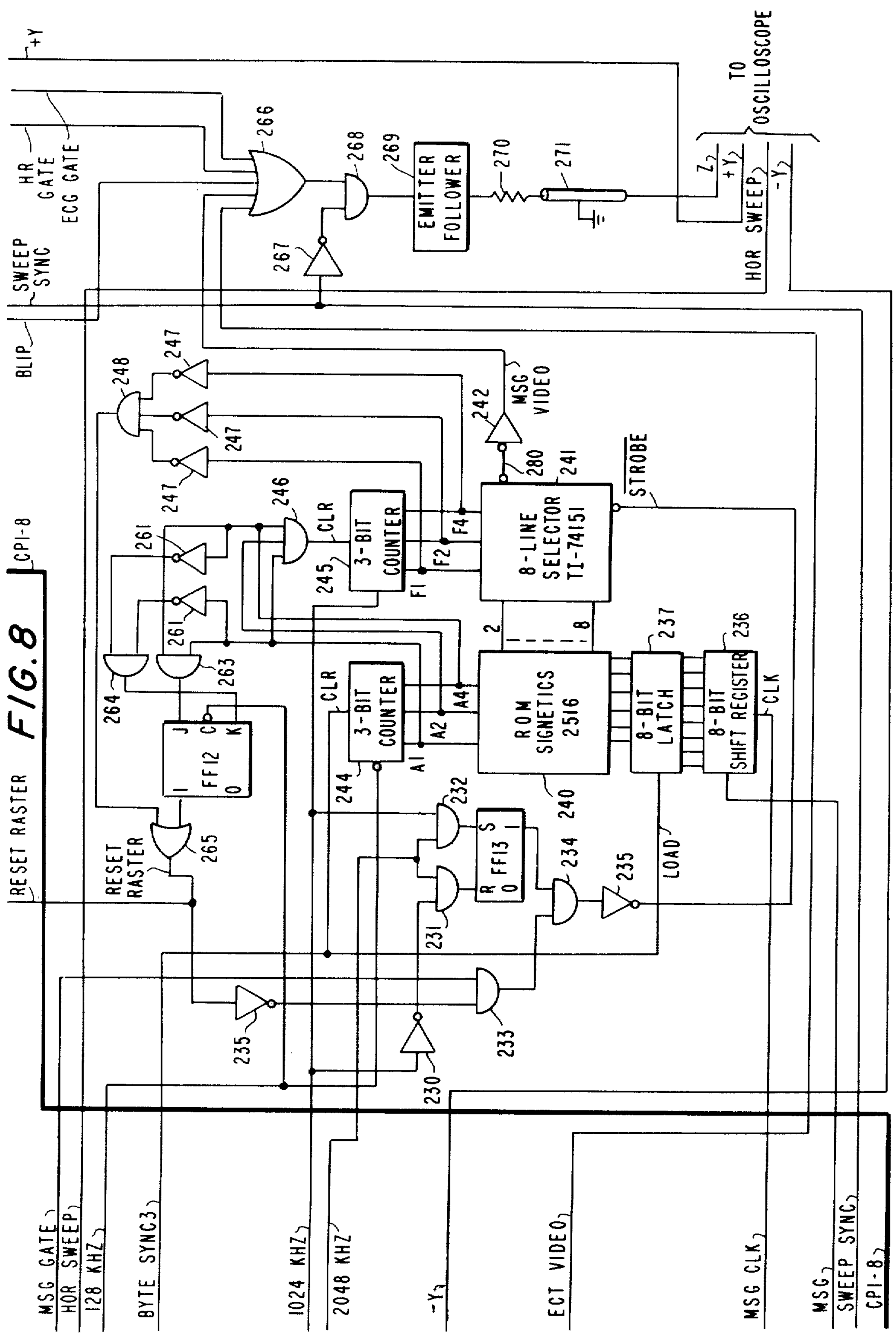

Most of the circuitry on FIG. 8 controls the formation of the message at the top of the display. The data bits on the MSG conductor, and the synchronized clock bits on the MSG CLK conductor occur at a 128-kHz rate. There are 32 character positions in the single-line message, and using a conventional ASCII CODE, 6 bits are required to identify each character. The character codes arrive in 8-bit bytes, with the last two bits of each byte being 0's. Thus 32 8-bit bytes are contained in the message data, for a total of 256 bits (the capacity of shift register 87 on FIG. 5). The 128-kHz clock rate insures that all of the character codes arrive at evenly spaced intervals within each 2-millisecond sweep across the display. Each 8-bit code is stored in shift register 236 on FIG. 8. The LOAD input of 8-bit latch 237 is energized by the BYTE SYNC3 pulses, one of which is generated following every eighth 128-kHz clock pulse. Accordingly, immediately after each character code is stored in shift register 236, the code is loaded in the 8-bit latch. Only the six least significant bits in the latch are extended to the address lines of read-only memory 240, since it is only a 6-bit code which is used to identify a character. (It will be apparent to those skilled in the art that all that is required is a 6-bit latch since the two most significant bits in each 8-bit byte are not used; however, in those cases where more than 64 different types of characters can be displayed, it may be necessary to use full 8-bit codes.)

FIGS. 19 and 20 illustrate the manner in which each character in the display is formed. FIG. 19 shows the organization of memory 240 for a single character. A 6×8 matrix is provided for each of the 64 different characters which can be formed, the 6-bit address in latch 237 serving to select one of the matrices in the read only memory (which, in this case, is a Signetics 2516 unit). Referring to the matrix shown in FIG. 19, it will be noted that the top row consists of six 0's as does the leftmost column. This is true for every character. It is the 5×7 sub-matrix which is actually used to define a character. The character shown in FIG. 19 is the letter S; each 1 in the matrix represents a dot which is to be formed on the display.

The display is formed by generating five raster sweeps, as shown in FIG. 20, and unblanking the Z axis whenever a dot is to be formed during a sweep. For example, the 7-bit code in column 1 of the matrix, looking upward, is 0100110. This means that during the first vertical sweep of the five used to form the letter S on the screen, and assuming that this sweep is divided into six equal parts, the Z axis must be unblanked during the second, fourth, and fifth parts of the sweep. The three resulting dots which are formed on the display are shown in the leftmost sawtooth of FIG. 20. Similar remarks apply to the other four sawtooths shown in FIG. 20 and columns 2-5 of the read-only memory matrix. It will be noted that the dots shown in FIG. 20 form the pattern which represents the letter S, it being understood that in the actual display the raster lines are more closely spaced in the horizontal direction, so that the dots more or less touch each other to form a continuous letter.

The 6-bit code in latch 237 selects a particular matrix within the read-only memory. The six columns in this matrix are accessed by the bit levels on address conductors A1, A2 and A4. The bit values represent the column address for the matrix (see FIG. 19). The three address bits cycle from 000 through 111. The address bits change, as will be described below, following each raster sweep; the cycling of the address bits is synchronized to the raster waveforms. The timing is such that eight raster sweeps could be provided as address bits A1, A2 and A4 cycle from 000 to 111. However, raster sweeps are not developed while the address bits represent the codes 000, 110 and 111. The five raster sweeps which are generated to form each character coincide with the addresses 001 through 101, the five addresses which access the five columns in the read-only memory which contain the dot-forming 1 bits. (The read-only memory provides 0 outputs on all eight of it output lines when address bits A1, A2 and A4 represent codes of 110 and (111.)

Referring to FIG. 8, the BYTE SYNC3 pulse which loads latch 237 with a new address also clears counter 244. The BYTE SYNC pulse is coincident with a negative step in the 128-kHz clock waveform which is applied to the count input of the counter. The counter is initially cleared and remains cleared until the following negative step in the clock waveform, at which time the count increments from 000 to 001. It is at this time that the first raster sweep is generated so that the accessed column 1 of read-only memory 240 can be used to form dots on the display. Since a BYTE SYNC3 pulse is generated following every eighth clock pulse in the 128-kHz waveform, and it is the PYTE SYNC3 pulse which loads latch 237, it is apparent that counter 244 cycles from 000 through 111 within the time that each character code is stored in latch 237.

Although the read-only memory has eight output lines, as shown on FIG. 19, the bits on output line 1 are not used. Accordingly, only output lines 2-8 are extended to 8-line selector 241 (Texas Instruments unit No. 74151). The Texas Instruments Unit No. 74151 is described in detail in the publication "The Integrated Circuits Catalog for Design Engineers" published by Texas Instruments, Inc., Publication No. CC401 10072–41-US, pages 9–339 through 9–350. What the selector does is to examine only one of the data input lines extended to it at any one time, and to energize its output line 280 depending upon the value of the bit on the examined input line. Which line is examined depends upon address bits F1, F2 and F4. The only time that the selector energizes its output conductor 280 in accordance with the bit value on the selected input line is when the STROBE conductor is low.

All three address lines A1, A2 and A4 for the read-only memory are extended to inputs of gate 246. Thus the gate operates to clear counter 245 when counter 244 represents a count of 111. The count input of counter 245 is connected to the 1024-kHz conductor. Since counter 245 has its count input pulsed at a rate eight times as great as the rate at which counter 244 has its count input pulsed, it is apparent that counter 245 cycles from 000 through 111 for each state of counter 244. It is this feature which allows selector 241 to examine each of its input lines in succession while the same column of the selected matrix in the read-only memory applies its respective bit values to the output lines.

Figure 18:
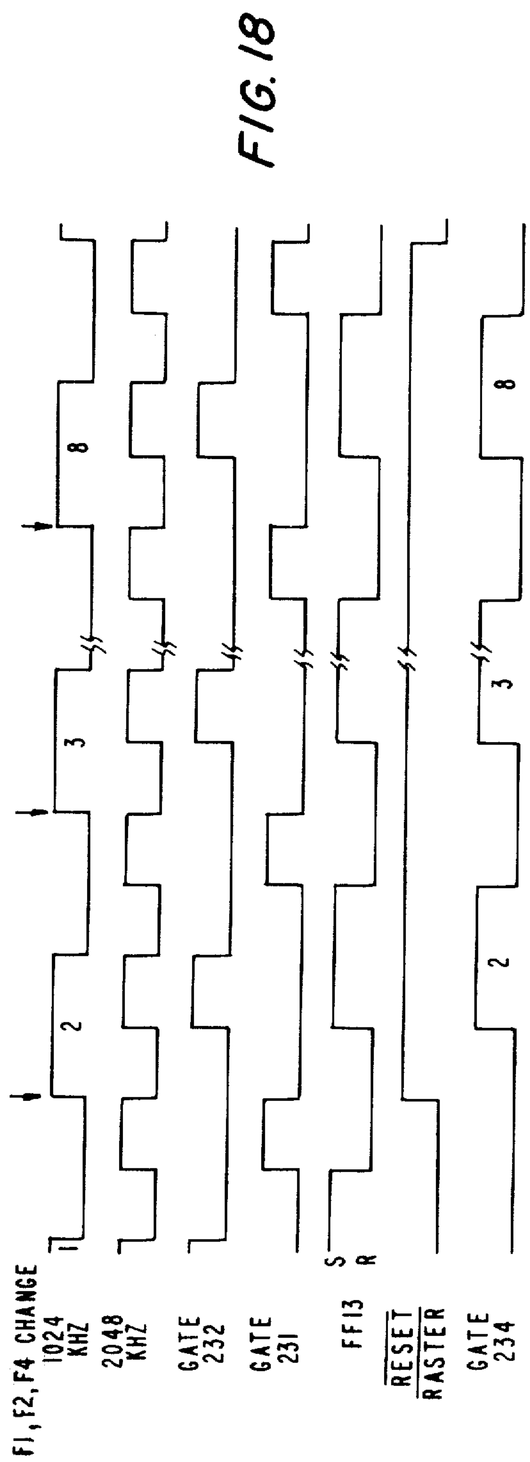
FIG. 18 depicts timing waveforms which will aid in understanding the operation of the display and keyboard logic and, in particular, the circuitry on FIG. 8.

The waveforms of FIG. 18 depict the operation of counter 245, selector 241 and the associated gates and flip-flop FF13 during the time that output conductors 2–8 of the read-only memory have stationary bit levels, that is, during a single raster sweep of FIG. 20. The 1024-kHz and the 2048-kHz waveforms are shown in FIG. 18; it will be recalled that it is the negative step in any higher-rate clock that controls a transition in a lower-rate clock. The 1024-kHz signal is applied to one input of gate 232 (FIG. 8) and inverter 230 provides a complementary signal at one input of gate 231. The 2048-kHz clock waveform is applied to the other input of each of gates 231 and 232. The output of each gate is high only when its two inputs are high, and FIG. 18 thus depicts the outputs of the two gates as functions of the two clock waveforms. Flip-flop FF13 is set in the 1 state whenever the output of gate 232 goes high, and it is reset in the 0 state whenever the output of gate 231 goes high. FIG. 18 depicts a waveform which indicates the state of the flip-flop as a function of the two gate waveforms.

One input of gate 234 is connected to the 1 output of flip-flop FF13. Consequently, the output of gate 234 can be high only when the flip-flop is in the 1 state. The other input of gate 234 is connected to the output of gate 233. One input of this gate is enabled by the MSG GATE conductor, and consequently gate 234 can operate (to control the formation of a message bit on the screen) only during those horizontal sweeps which are used to form the message. The other input to gate 233 is derived from the RESET RASTER waveform through inverter 235. Consequently, gates 233 and 234 operate only when the RESET RASTER waveform is low. As will be described below, the RESET RASTER waveform is low only during each of the five raster sweeps used to form each message character. FIG. 18 shows the RESET RASTER waveform at the output of inverter 235. The selector can be strobed in order to form a dot on the screen only when this waveform is high.

Figure 17:
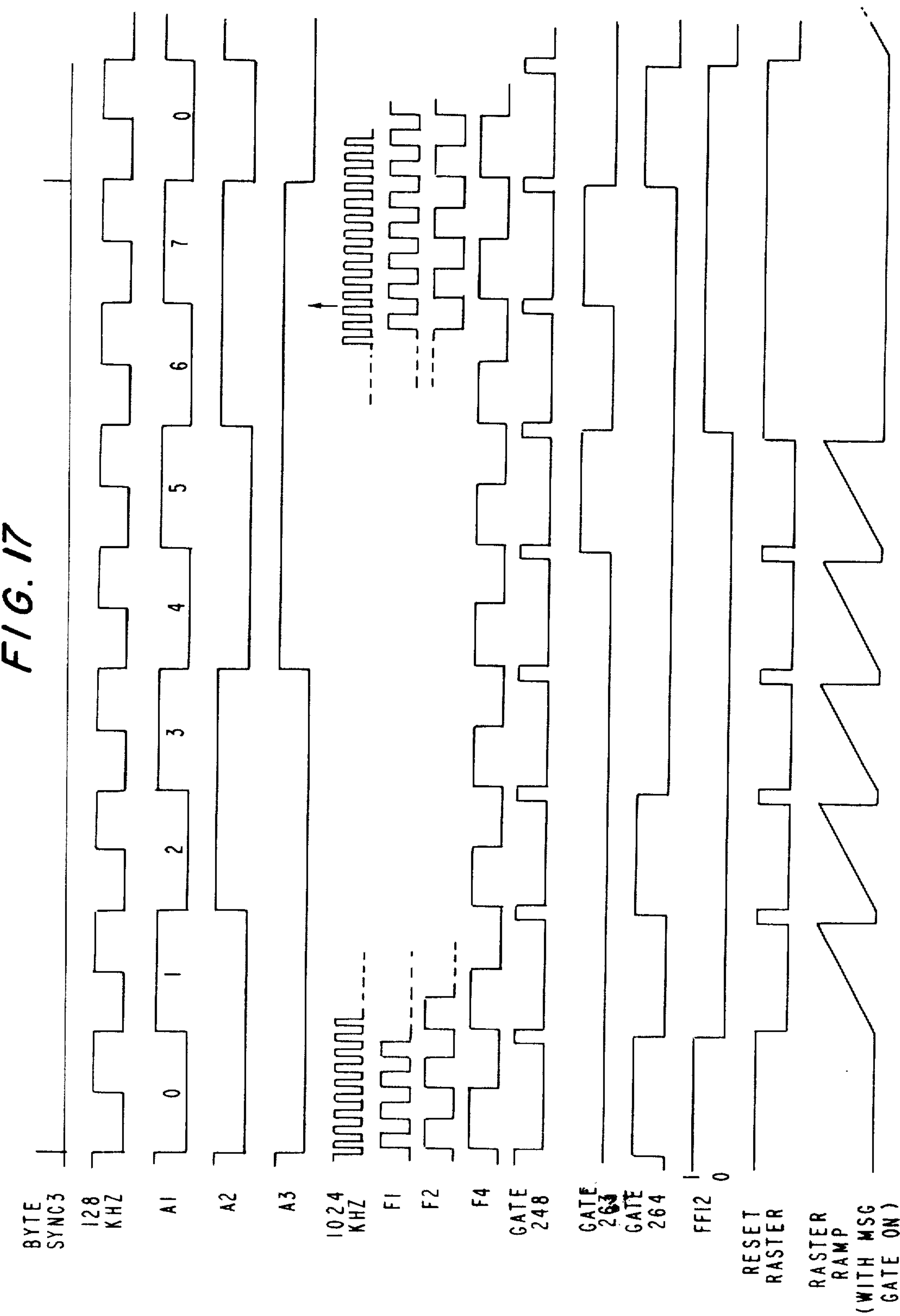
FIG. 17 depicts timing waveforms which will aid in understanding the operation of the display and keyboard logic and, in particular, the circuitry on FIGS. 8 and 11.

With reference to FIG. 17, it will be shown that the RESET RASTER waveform does not go low to permit the formation of message dots until after address bits F1, F2 and F4 have cycled from 000 to 001. The 1024-kHz clock pulses on FIG. 18 are labeled 1–8 corresponding to the F1, F2, F4 codes 000 through 111, it being noted that each positive step in the 1024-kHz clock waveform changes the count of counter 245. This is indicated by the very top line of FIG. 18 where the changing of address bits F1, F2 and F4 is indicated by the arrows. During the first clock waveform of each cycle of eight, counter 245 represents a code of 000. Since the RESET RASTER waveform does not go high until a count of 001 is reached, the waveform is shown going high at the start of cycle 2 in FIG. 18. The waveform goes low once again only when the three address bits F1, F2 and F4 represent a 000 code at the start of the next cycle.

Since the output of gate 234 can go high only when the RESET RASTER waveform is high and flip-flop FF13 is in the 1 state, the output of the gate goes high at a 1024-kHz clock, the output of gate 234 goes high only seven times. It is when the output of this gate is high that selector 280 energizes its output conductor 280 depending upon the value of the bit on one of input lines 2-8. The fact that gate 234 does not go high when address bits F1, F2 and F4 represent a 000 code is of no moment because the top row of every read-only matrix see FIG. 19) consists of six 0's and output line 1 from the read-only memory need never be examined by selector 241. Inverter 235 is provided since selector 241 is operative only when its STROBE input is low. The bit level on conductor 280 is low when a 1 is read on a selected input line by the selector. Consequently, inverter 242 is provided to apply a high level on the MSG VIDEO conductor when a 1 bit is read, that is, when a dot is to be formed in the message. The MSG VIDEO conductor is extended through OR gate 266 to control the formation of a dot on the display, as described above.

It should be noted that the selector is not strobed simultaneously with the changing of address bits F1, F2 and F4. Instead, it is only during the middle half of the duration of each state of counter 245 that the selector is strobed. This permits address lines F1, F2 and F4 to settle prior to the selector strobing.

Although the STROBE input of the selector is pulsed seven times during each cycle (see FIG. 18), during the last two strobes of the selector all eight outputs of the read-only memory represent O's; this is the way the memory operates for A1, A2 and A4 codes of 110 and 111. Consequently, it is not necessary to inhibit the generation of the last two selector STROBE pulses. (It is not really necessary to inhibit the first STROBE pulse in each cycle either because for an A1, A2, A4 code of 000, the first matrix column is selected and it contains 0's only. But it certainly does no harm to inhibit the first STROBE pulse which would otherwise occur.)

FIG. 17 depicts the manner in which the RESET RASTER waveform is formed. It will be recalled that the RESET RASTER signal is extended to an input of gate 208 on FIG. 11 to control only five raster sweeps during the formation of each message character. As shown on FIG. 17, it is when the RESET RASTER waveform is low that the raster ramps can be formed (provided that the MSG GATE signal is high, that is, provided that the horizontal sweep in progress is being used to form the message, since the other input to gate 208 is the MSG GATE signal). Furthermore, as described in connection with selector 241, when address bits A1, A2 and A4 represent a 000 code, the RESET RASTER signal remains high so that gates 233 and 234 do not operate to strobe the selector in each cycle until address conductors A1, A2 and A4 have advanced to represent a 001 code.

FIG. 17 depicts two BYTE SYNC3 pulses, each of which clears counter 244 (FIG. 8). The counter changes state with each negative step in the 128-kHz waveform. FIG. 17 shows the cycling of address bits A1, A2 and A4 with the 128-kHz clock.

FIG. 17 also shows the 1024-kHz clock waveform together with the cycling of the F1, F2 and F4 bit outputs of counter 245 (FIG. 8). It will be recalled that the counter is cleared when the output of gate 246 first goes high — when address bits A1, A2 and A4 represent a code of 111. This occurs at a time shown by the vertical arrow in the A3 waveform on FIG. 17. At this time, the counter should be in the 000 state anyway during orderly cycling of the system. The clear input to counter 245 is required in order that when the system is first turned on, the cycling of counter 245 be synchronized with a new count in counter 244.

Each of the F1, F2 and F4 lines is extended through a respective inverter 247 to an input of gate 248. Consequently, the output of gate 248 goes high only when all three address bits are 0, as shown in FIG. 17. The output of the gate is extended to one input of OR gate 265. Thus whenever the output of gate 248 goes high, the RESET RASTER waveform is similarly high. This is shown in the next-to-last waveform of FIG. 17. It is flip-flop FF12 which causes the RESET RASTER waveform to be high at other times.

The two inputs of gate 263 are connected to the A1 and A4 address lines. Consequently, the output of gate 263 is high only when both A1 and A3 are high, as shown in FIG. 17. The same two address lines are connected through inverters 261 to the inputs of gate 264. Consequently, the output of gate 264 is high only when both address lines are low, as shown in FIG. 17. The output of gate 263 is connected to the J input of flip-flop FF12 and the output of gate 264 is connected to the K input of the flip-flop.

The 128-kHz clock pulses are applied to the clock input of flip-flop FF12. The clock changes state only coincident with the falling edge of a clock pulse, depending upon the levels at the J and K inputs. Assume that flip-flop FF12 is initially in the 0 state. In order for the flip-flop to be switched to the 1 state, the J input must be high and the K input must be low when the clock input goes low. When address line A1 goes high at the start of cycle 5 in FIG. 17, the output of gate 263 goes high (at which time the output of gate 264 remains low). The 128-khz waveform is shown going low at this time. However, since it is the 128-kHz clock which causes bit A1 to change in the first place, it is apparent that the output of gate 263 does not go high until shortly after the clock pulse waveform goes low. Since flip-flop FF12 can change state only during a negative step in the clock waveform, the negative step in the clock waveform shown in FIG. 17 as being coincident with the output of gate 263 going high does not control a change in the flip-flop state. However, the next negative step in the 128-kHz clock waveform, although it causes the A1 line to go low and the output of gate 263 to similarly go low, appears at the clock input of the flip-flop while the J input is still high. Consequently, it is at the trailing edge of the first positive pulse at the output of gate 263 that flip-flop FF12 switches to the 1 state.

The only way that the flip-flop can be switched back to the O state is when the K input is high and the J input is low. This state comes to pass with the next BYTE SYNC3 pulse. However, since it is the negative step in the 128-kHz clock waveform which causes the output of gate 264 to go high and the output of gate 263 to go low, these two gate outputs do not actually change until shortly after the negative step in the clock waveform has appeared at the clock input of the flip-flop. Consequently, there is no change in the flip-flop state. Instead, it is the next negative step in the clock waveform (the same step which causes the output of gate 264 to go low as soon as the A1 bit changes in value) which resets flip-flop FF12 in the O state. This is shown occurring at the end of the first of the eight cycles between successive BYTE SYNC3 pulses on FIG. 17.

Since the 1 output of flip-flop FF12 is connected to the second input of OR gate 265, it is apparent that the RESET RASTER waveform is high when either flip-flop FF12 is in the 1 state or the output of gate 248 is high. This is shown in FIG. 17. As described above, the RESET RASTER waveform goes low for only five of the eight cycles between successive BYTE SYNC3 pulses because only five rasters need be generated to form each character, and the first time that the RESET RASTER waveform goes low is at the start of the second of the eight cycles.

Organization Of Data And Its Orderly Transmission To the Display And Keyboard Logic The data for each patient can be stored in a conventional core or semiconductor memory, or a memory of some other type. The display and keyboard logic would simply have to properly address the memory whenever new data is required. However, a far more economical approach is to store the data on a disk and to have a computer retrieve data from the disk and then forward it to the display and keyboard logic. This is especially true in those cases where the computer is used to monitor a patient for deriving the data in the first place. In such a case, the data would be typically stored on a disk, and the data can be retrieved at little additional cost by utilizing the equipment already provided for other purposes.

The Disk Storage

A disk in an RKO5 disk drive (FIG. 1) has many tracks on it for containing data. Each track has 12 sectors and there are 256 16-bit words in each track sector. Since the data used by the display and keyboard logic is operated upon in 8-bit bytes, it is also convenient to think of the successive data bits in each sector as representing 512 8-bit bytes. In the illustrative embodiment of the invention, the data for each patient is stored in 258 successively numbered sectors. The first sector for each patient contains the trend data. It will be recalled that the trend data for each patient has two values for each minute of patient monitoring, one 8-bit value representing the number of heartbeats which were detected during that minute of monitoring and the other 8-bit value representing the number of ectopic beats which were detected during that same minute. The two types of trend data alternate, as described in connection with FIGS. 4 and 5. Since 256 16-bit words can be stored in a single sector, and a 16-bit word is required for each minute of monitoring, it is apparent that slightly more than four hours of trend data can be stored in each patient's trend data sector.

The second sector used for each patient is basically an address table the entries in which identify particular ones of the last 256 sectors provided for the same patient. It will be recalled that each 4-second waveform (plus message) recorded for a patient is represented by 512 8-bit bytes. Since this is the bit capacity of each sector on the disk, each sector can contain only the data required to display a single 4-second ECG signal segment. The number of 4-second waveforms which are stored on the disk for each patient (and therefore the number of waveforms which can be retrieved and reviewed on the display) depends on how many sectors are allocated to each patient for the storage of ECG data. In the illustrative embodiment of the invention, 256 sectors are allocated to each patient for the storage of ECG waveform data. (In other words, it is assumed that in the usual case there will be no more than 256 4-second ECG signal segments of interest which will have to be recorded for subsequent review during any monitoring period of approximately 4-hour duration.) In order to control the display of all ECG waveforms which were recorded during any particular minute of monitoring, the system must be able to identify the successively numbered sectors which contain ECG data for the selected minute. It is the function of the table sector for each patient (the second of the 258 sectors allocated to each patient) to identify which of the following 256 sectors are associated with particular 1-minute intervals. A table of this type is required because there is no one-to-one correspondence between each sector of ECG data and a respective minute in the 256 minutes of monitoring. There may have been some 1-minute intervals during which no ectopic beats were detected and therefore no ECG data recording took place, while there may be other 1-minute intervals during each of which several 4-second ECG signal segments were recorded.

FIG. 24 depicts the organization of a typical patient table sector. The table contains 256 locations. The left column in FIG. 24 represents the addresses 1-256 within the sector. Any non-zero 16-bit word stored at an address represents a sector address. Each of the 256 positions (left column) corresponds to a respective 1-minute interval of monitoring. A non-zero data value at that position identifies the sector associated with the patient which contains the samples of the first 4-second ECG signal waveform recorded during the respective minute. Any zero entry in the right column of FIG. 24 indicates that no ectopic beats were detected during the respective minute and therefore that no 4-second ECG signal segments were recorded. This will become clearer upon considering the specific example illustrated in FIG. 24.

It is assumed that the first of the 258 sectors associated with a particular patient has an address N. The trend data for that patient is stored in this sector. That same patient's "table" (FIG. 24) is stored in sector N+1 and his successively recorded ECG data is stored in sectors N+2 through N+257.

At location 1 in sector N+1 there is stored a data value of 0. This means that during the first minute of monitoring, ectopic beats were detected and no ECG waveform data was recorded. At location 2 of sector N+1, which corresponds to the second minute of patient monitoring, there is an entry of N+2. Any such non-zero entry implies that at least one ectopic beat was detected during the respective minute. The data value represents the address of the first sector associated with the patient which contains the data of a 4-second ECG signal segment. Since the first ECG data sector for the patient has an address N+2, the first non-zero data value stored in a patient table sector is always N+2.

But the storage of the value N+2 at address 2 of the patient table sector gives no indication of how many 4-second recordings were made during the respective second minute of monitoring. To determine this, it is necessary to look at the next entry in the table. At address 3 in the patient table sector, there appears the data value N+3. This means that during the third minute of monitoring at least one ectopic beat was detected, and the first ectopic beat detected during this 1-minute interval has its respective 4-second recording represented in sector N+3. Since the previous table entry is N+2, it is apparent that during the second minute of monitoring (corresponding to address 2 in the patient table sector) only a single ectopic beat was detected because only sector N+2 was used to store ECG data for that minute of monitoring. It is apparent that in order to determine how many 4-second segment recordings were made for any 1-minute interval, two successive non-zero data entries of the patient table sector must be examined to determine their difference.

During the fourth minute of monitoring (correspond-ıg to address 4), an ectopic beat was also detected. he first recording made for this 1-minute interval ppears in sector N+5. It is thus apparent that during ıe third minute of monitoring (corresponding to ad-ress 3 for which there is a data entry of N+3), there ere two ectopic beats detected, and thus sectors N+3 nd N+4 were used for recording during the third min-te of monitoring.

At address 5 of the patient table sector there is a data alue of 0. This means that no ectopic beats were de-ected during the fifth minute of monitoring. Similar emarks apply to address 6 of the table.

At address 7 there is an entry of N+9. This means ıat during the seventh minute of monitoring at least ne ectopic beat was detected and the first ectopic beat esulted in a 4-second recording being made in sector I+9. Referring to the nearest preceeding non-zero ntry, it is apparent that during the fourth minute of ıonitoring (corresponding to address 4 in the table), our ectopic beats were detected because four sectors ere used to store four different 4-second recordings, hese sectors having addresses N+5, N+6, N+7 and I+8.

In a similar manner, the storage of the value N+12 at ddress 8 of the table sector implies that during the ighth minute of monitoring at least one recording was nade and the first such recording is contained in the ector whose address is N+12. The same entry further mplies that during the seventh minute of monitoring corresponding to address 7) three 4-second ECG sig-ıal segments were recorded, namely, in sectors N+9, N+10 and N+11.

Once it is understood how the data in each patient able sector identify the ECG data sectors which con-ain 4-second signal segments corresponding to respec-ive ones of the 256 minutes of monitoring, it is rela-ively straightforward to appropriately program the computer so that the proper data is read from the disk and then transmitted to the display and keyboard logic circuit as it is required. As described above, when the physician wishes to observe a new ECG waveform, he operates the display key on the keyboard. This, in turn, results in a signal being transmitted over conductor REQA to the DR11-A general purpose interface for informing the computer that some action is required. The various flow charts of FIGS. 21A through 23B set forth the steps performed by the computer in servicing the request.

The Display Service

The entry point in the flow chart of FIG. 21A is labeled DSPSRV, which represents "display service". The first step taken by the computer is to disable the REQA interrupt facility. This means that no further physician requests for a display will be serviced until the present one has been taken care of. The computer reads the data word on input lines IN 0–15. After the data is read, conductor DTR is pulsed by the general purpose interface. Referring to FIG. 4, it will be recalled that the pulsing of this conductor after input data is read causes flip-flop FF4 to be reset. This is preparatory to a subsequent request for service which results in the setting of the flip-flop. (If the physician immediately operates the display key before the new display is formed, flip-flop FF4 is once again set and the REQA line goes high. However, the service request will not be handled until after a new waveform is displayed on the screen and the REQA interrupt facility is once again enabled.)

Trend Display

The system then checks the patient identification code on input lines IN 3, IN 4 and IN 5 to see if the patient identification number has changed since the last service request. A patient identification word ECG-NUM is maintained to identify the current patient identity. If the present patient number is not the same as the previous patient number, a branch is made to the DSPTND program (FIG. 23A) to control the display of new trend data. If the physician is now interested in a new patient, it is his trend data which must be displayed rather than that of the previous patient. Assuming, however, that what is required is the display of the next ECG waveform of the same patient (and therefore no change in the trend plots), a test is made to determine the state of the display and keyboard logic circuit. It will be recalled that the state of the system is represented on input lines IN O and IN 1. This system should be in state 84 at this time during normal operation. If the system is not in state S4, for example, if power has just been turned on and the system is in an intermediate state, a branch is made to the DSPTND program in order to "start at the beginning" for the patient, that is, to display his two respective trend plots.

b. ECG Display

But assuming that the system is in state S4, steps are initiated for loading a new sector of ECG waveform and message data in shift registers 75 and 87 (FIG. 5). Since the data for an ECG waveform (and associated message) can only be loaded in the shift registers when the system is in the state S3, the computer, via the DR11-A general purpose interface, transmits a 011 code on output conductors OUT 13, OUT 14 and OUT 15. The data word is transmitted together with the pulsing of conductor NDR. With reference to FIG. 4, it will be recalled that the transmission of a 011 code causes the system to be set in state S3 at which time ECG and message data can be loaded in the respective shift registers.

c. Table Lookup

It may be that since the last time the physician operated the display key, he operated the cursor key so that the cursor moved to the right across the screen. The present cursor position must be determined before it is possible to identify a particular waveform for display. The CRSPOS word represents the previous cursor position for the patient. It will be recalled that the present cursor position appears on data input lines IN 6 through IN 13. A test is performed to see if the present cursor position differs from the previous position represented by CRSPOS. If it does, the system sets the NEWCP word equal to 1 (it is otherwise a 0) to indicate that the cursor position has changed since the last service request. At the same time, the CRSPOS value is set equal to the actual (new) cursor position. After NEWCP has been set equal to 1 and CRSPOS has been updated if necessary, the first step in controlling the display of a new ECG signal segment is to retrieve all of the data in the respective table sector of the current patient from the disk. The computer first "sets up" the disk; this simply entails informing the disk interface and the RKO5 disk drive that a complete sector is to be read. Then the address of the sector is transmitted. With reference to FIG. 24, the address of each patient table sector is the second of the patient's 258 sectors, in the example of FIG. 24 address N+1. This address is transmitted to the RKDA register within the disk drive — a standard operation whenever data on a disk is to be read.

But before the reading of the disk actually begins, a return address must be set up. While the 256 16-bit words are read from the disk, the computer can proceed to do other work if necessary. Accordingly, it is standard practice to note the address of the first instruction in the subroutine which is to be executed after the data is retrieved from the disk. In this case, the return address identifies the start of the DRET 1 subroutine (FIG. 21B). After the return address is set up, a command is given to start the reading. Following reading of the table sector of the current patient and its storage in the computer memory, a return is made to the main program, which then initiates a branch to the DRET 1 subroutine.

The first step in this subroutine (FIG. 21B) is to store the CRSPOS word in register R1. This word identifies the current position of the cursor, the CRSPOS word having been updated (FIG. 21A) in the event the cursor position was moved subsequent to the last service request. A test is then made to see if NEWCP is equal to 1. This 1-bit word has been set equal to 1 previously (FIG. 21A) only if the cursor position has been changed.

The maximum number of waveforms which can be recorded on the disk is 256. As the cursor is moved to the right, time successive waveforms can be displayed. But it is possible that the cursor will be moved to a point which references a time before which 256 waveforms were already recorded. In other words, it is possible that the ECG waveform storage capacity for a patient can be exhausted before 256 minutes of monitoring have elapsed. In such a case, for the present cursor position (and all higher positions) there are no more waveforms available for display. Whenever this kind of "END" condition is reached, as will be described below, an "END" message is displayed. It is controlled by switching the LSTONE word from a 0 to a 1.

The value of ECGADR is the address of the sector which immediately follows the sector whose samples were last displayed. (The address ECGADR is transmitted to the RK11-C interface to retrieve a sector of data. The interface automatically increments the ECGADR value, as is known in the art, after a sector of data is retrieved. Thus ECGADR, at the start of the program, represents the next sector address.) When an "END" message is displayed, the waveform with it, if any, may be selected arbitrarily; the only thing of significance is the message. Thus any valid ECGADR value may be used to retrieve ECG data. But the current value should not be used if it is N+258, since the last ECG data for a patient is contained in sector N+257. Since ECGADR may sometimes equal N+258, the current value of ECGADR is always decremented prior to the display of an "END" message to insure that a sector not associated with the current patient is not accessed.

The CRSPOS word is used to examine one of the 256 entries in the table sector. With reference to FIG. 24, suppose that the present value of CRSPOS is 3 and it did not change since the previous display service routine was executed (NEWCP=0). Suppose further that during the previous execution of the display service routine it was the first (N+3) of the two sectors which contain 4-second signals recorded during the third minute of monitoring whose data were retrieved. At the end of the display of the waveform, the ECGADR address was incremented to N+4. Thus ECGADR now points to an ECG sector which is associated with minute 3 of monitoring. But suppose that it was sector N+4 which was previously accessed. In this case ECGADR, which now has a value of N+5, points to an ECG sector associated with a different minute of monitoring. (In this case, it is minute 4, but in general the present value of ECGADR can point to a sector associated with a non-successive minute.) Thus based only upon the CRSPOS and ECGADR values, the system cannot determine whether ECGADR points to a sector which contains an ECG waveform that was taken during the minute of monitoring represented by CRSPOS or some other minute. For this reason, it is necessary to examine the next non-zero entry in the table which follows the non-zero entry at location CRSPOS.

If NEWCP=0, register R1 is incremented (FIG. 21B). A test is then performed to see if R1 exceeds 256. The reason for this test will be described below, but assume now that R1 is less than 256. In the example under study, the number 3 stored in register R1 is thus incremented to 4. Since R1 (3) does not exceed 256, a test is then performed to see if R1 points to a non-zero entry, which in this case it does (N+5). If it does, a branch is made to point A on FIG. 22A at which time a test is made to see if the non-zero value (N+5) exceeds the value of ECGADR. If it does, it means that the sector pointed to by ECGADR, which in this example must be sector N+4, contains data which was taken during the same minute of monitoring represented by CRSPOS. Accordingly, a branch is taken directly to location EREAD; the present value of ECGADR is used to retrieve the next waveform for display. There is no need to set up procedures for advancing the cursor on the display (which requires setting ADVCTR to an appropriate value) because the actual position of the cursor on the screen represents the minute of monitoring during which the ECG waveform now to be displayed (represented by ECGADR) was actually taken.

After the data in sector N+4 is displayed, ECGADR is automatically incremented to N+5. During the next execution of the display service routine, and assuming that the cursor position has not been changed by the physician so that NEWCP=0, after CRSPOS (3) is stored in register R1, it is incremented to 4. Once again R1 points to a non-zero entry so a test is then performed (FIG. 22A) to see if this entry exceeds ECGADR. Since the entry at location 4 of the table is N+5 and this is the same value represented by ECGADR, the answer to the test is in the negative. Thus the value of CRSPOS (3) is subtracted from the value stored in register R1 (4), and the ADVCTR word is set equal to the difference (1). This word represents the number of positions by which the cursor must be moved under automatic control. With reference to the table of FIG. 24, it will be seen that sector N+5 contains data which was taken during the fourth minute of monitoring. Since the cursor position on the screen identifies the third minute, the cursor must be advanced one position.

As another example consider the case in which the value of CRSPOS is 4 (with NEWCP still being 0). With reference to FIG. 24, it will be noted that four ECG waveforms were recorded during the fourth minute of monitoring, while during the fifth and sixth minutes of monitoring no ectopic beats were detected.

After the first ECG waveform taken during minute 4 and whose data is stored in sector N+5 is displayed, the value of ECGADR is incremented to N+6. During the next execution of the display service routine, when the contents of R1 are incremented, R1 assumes a value of 5. Since R1 does not now point to a non-zero entry, R1 is incremented once again to a value of 6. Since this value also does not point to a non-zero entry in the table, R1 is incremented to a value of 7. It is the non-zero entry (N+9) at address 7 in the table sector which must be used to determine how many sectors are associated with the fourth minute of monitoring.

During the first four display service routines which are executed when CRSPOS has a value of 4, the values of ECGADR are N+5, N+6, N+7 and N+8. Since N+9 is greater than all of these values, the test at point A (FIG. 22A) results in a branch being taken directly to EREAD. But after the display of the data stored in sector N+8, ECGADR is automatically incremented to a value of N+9. During the next execution of the display service routine, it is found that the non-zero entry (N+9) pointed to by register R1 (which is incremented, as in the previous four executions of the same routine, to a value of 7) does not exceed the value of ECGADR (which is now N+9). This means that the present cursor position (identifying the fourth minute of monitoring) is not the minute during which the ECG waveform stored in sector N+9 was taken. Consequently, the value of CRSPOS (4) is subtracted from the value stored in register R1 (7). This operation results in ADVCTR being set equal to 3. Thus, as will be explained below, the cursor will be advanced three positions to position 7 on the display so that it will identify that minute of monitoring (7) during which the next ECG waveform to be displayed actually occurred.

On FIG. 21B it will be noted that after the value of R1 is incremented, the new value is always checked to see if it exceeds 256. If it does, the system simply displays an "END" message by first setting LSTONE to a 1 and decrementing ECGADR for the reason described above. The test is required to insure that R1 does not reference a minute (cursor position) past the maximum value of 256 (corresponding to a count of 255 in counter 50 of FIG. 4).

Figure 22A:
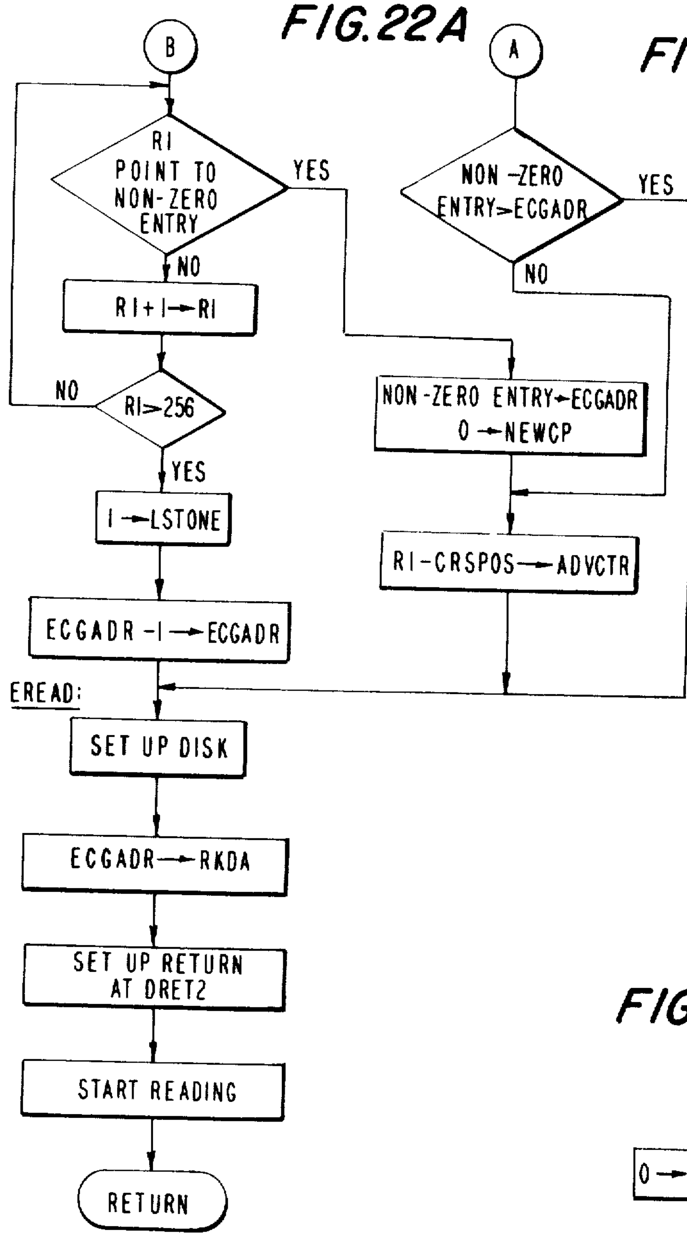

Thus far it has been assumed that NEWCP=0. But if NEWCP=1, i.e., the cursor position has changed since the last service request, the test for checking the value of NEWCP (on FIG. 21B) results in a branch being taken to point B (FIG. 22A). But it may be that during the minute identified by the physician, no ectopic beats were detected; CRSPOS may point to an address in the table which has a 0 data value. Thus at point B, a test is performed to see if CRSPOS points to a non-zero value.

For example, suppose that for the patient whose table sector is that shown in FIG. 24 the value stored in register R1 is 5. In such a case, R1 does not point to a non-zero data value. Accordingly, the test result is negative and, as shown in FIG. 22A, the value of R1 is incremented. With the value 6 now stored in the register, when the test is reexecuted a negative answer is obtained once again. Consequently, R1 is incremented again to a value of 7. This time, R1 points to a non-zero entry (N+9) and the program advances to the next step. During this procedure R1 is always tested to see if it exceeds 256. If it does, the previously described steps for setting up an "END" message are taken.

The non-zero entry (N+9, in the example under consideration) is used to set ECGADR. At the same time, the NEWCP word is switched back to a 0 to initialize it for the next service request.

Since the cursor position has been changed (NEWCP was a 1), the previous value of ECGADR (the address of the next sector whose data would otherwise have been displayed had the cursor not been moved) is irrelevant to the system operation. Thus after the new cursor position is stored in register R1, R1 is incremented, if it must be, until it points to a non-zero entry in the table. That entry represents the address of the sector whose ECG data should be displayed. It is for this reason that the entry (N+9, in the example considered above) is used to set the ECGADR word. But the address in the table sector which contains this non-zero value will not equal CRSPOS in the event R1 was incremented. Thus if the cursor is not actually advanced on the screen under automatic control, it will identify a particular minute interval which is not the interval which contained the ECG waveform which will be displayed. Accordingly, the difference between the incremented value in register R1 and the CRSPOS value is derived and used to set ADVCTR. This difference will be used subsequently to control the automatic advance of the cursor. The system then proceeds to EREAD.

d. Filled Disk

There are only 256 sectors for each patient which contain ECG data. If these sectors are all filled during the early part of monitoring, the entries at the end of the table will all be 0's; even if an ectopic beat was detected, since the associated waveform could not be stored the entry in the table for the respective minute must be a 0. What happens in such a case is that R1 is incremented continuously while the system looks for a non-zero entry. Since such an entry is not found, R1 is eventually incremented up to 257, and an "END" message is displayed. This is the desired effect since there is no waveform which can be displayed. Any waveform which is displayed is disregarded; it is the message which is important. The message informs the physician that there are no more waveforms which can be displayed for the present cursor position and all higher positions.

e. Reading ECG Data from Disk

Once the system reaches point EREAD (FIG. 22A), the value of ECGADR is the sector address which contains the data for the ECG waveform which is to be displayed. This data must first be retrieved from the disk. The disk drive is set up by informing it that a complete sector is to be read, and the sector address, represented by ECGADR, is transmitted to register RKDA. So that the computer can perform other work during the disk reading, if such work is to be performed, a return address at DRET2 is set up. Reading is then commenced. After the complete sector has been read, a return is made to the main program.

Figure 22B:
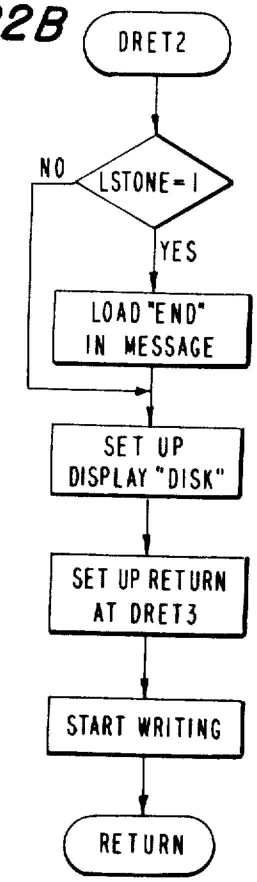
Figure 22C:
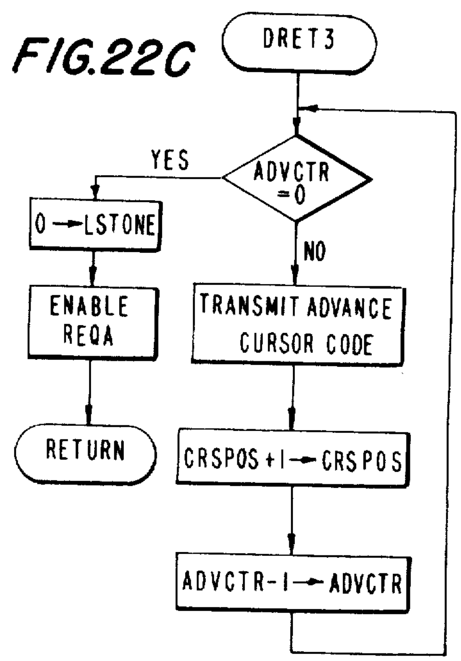

The main program then causes a branch to be taken to the return address DRET2 (FIG. 22B). The 512 8-bit bytes now stored in the computer memory represent both the message to be displayed and the ECG data samples. Each message consists of 32 8-bit ASCII character codes. Referring to FIG. 2, it will be noted that the majority of these character codes represent blank spaces. In fact, there are only 14 non-space codes. At the center of the message there is a 3-letter waveform description (VPB in the example shown)

which provides some information about the displayed waveform. This information can be derived, for example, in the two systems disclosed in my above-identified applications, and the appropriate code stored on the disk so that the appropriate message can be displayed subsequently. However, the 3-letter message is changed to "END" when the need for this has been determined previously, resulting in the setting of LSTONE to a 1. All that this operation entails is the storage of three new 8-bit ASCII codes in place of the three codes whose letters would otherwise describe the waveform to be displayed.

After the system finishes reading the disk sector and branches to the DRET2 subroutine, the value of LSTONE is examined. If it is a 1, the word "END" is stored in the message, and the system then proceeds to set up the display "disk". On the other hand, if the value of LSTONE is 0, a branch is taken directly to that point where the display "disk" is set up.

f. Sending ECG Data to Display

At this point the disk interface controls a "write" operation; the computer and the disk interface operate as though a disk sector is being written. Of course, the function of the display interface of FIG. 3 is to "fool" the disk interface; the disk interface operates as though it is writing into a disk sector, while in actuality it is merely transmitting 512 8-bit bytes to the display and keyboard logic. The step of setting up the display "disk" simply refers to the fact that the disk interface is set up to operate in the write mode. The DRIVE SEL E conductor is energized (see FIGS. 1 and 3), and the disk interface is informed that 4,096 bits are to be forwarded to the display and keyboard logic (which is treated as a disk drive). Ordinarily, the disk interface must be given a sector address to control writing of the data in the proper sector. In this case, however, an arbitrary address can be given since the data bits are simply transmitted serially to the display and keyboard logic through the display interface.

Before the data is actually transmitted, a return address at DRET3 is set up. The system then starts "writing" which simply means that it transmits data bits to the display and keyboard logic.

After the write operation is over, a return is made to the main program, at which time subroutine DRET3 (FIG. 22C) is executed. Although the new ECG waveform has been displayed, the cursor position has not yet been moved. A test is performed to determine the value of ADVCTR, and if it is a 0, a branch is taken to the step in which LSTONE is set to a 0. This is necessary preparatory to another service request in the event LSTONE was previously a 1. It will be recalled that the first step executed in the display service routine was the disabling of the REQA interrupt facility. Since the display service routine has now been fully executed, the interrupt facility is now enabled so that the display service routine can be executed once again if the display key is operated. A return is then made to the main program.

On the other hand, if the valve of ADVCTR is not 0, the system transmits an advance cursor code (111) on output lines OUT 13, OUT 14 and OUT 15. Referring to FIG. 4, it will be recalled that this code causes counter 50 to increment so that the cursor will be advanced one position to the right on the screen. In the next step in FIG. 22C, the value of CRSPOS is incremented. This is necessary so that CRSPOS will represent the actual position of the cursor on the screen. The value of ADVCTR is then decremented and a test is once again performed to see if it equals 0.If it does, the cursor need not be advanced anymore. But if the value of ADVCTR is not 0, the cursor is advanced one position again, the value of CRSPOS is incremented, and the value of ADVCTR is decremented. This process continues until eventually the value of ADVCTR is 0 and an exit is made from the subroutine after setting LSTONE to a 0 and enabling the REQA interrupt facility.

g. Reading Trend from Disk

Referring back to FIG. 21A, it will be recalled that whenever the patient number has been changed or the system is not in state S4 when a service request is made, a branch is made to the display trend (DSPTND) subroutine. This subroutine is shown on FIGS. 23A and 23B. The first step in the subroutine is to update ECGNUM with the new patient number. The disk interface is then set up to control the reading of the new patient's first sector in order to retrieve the trend data. In the case of the example shown in FIG. 24, sector address N is transmitted to register RKDA in the disk interface. A return address at TND1 is then set up, and reading of the patient's trend sector is commenced.

h. Trend to Display

Following retrieval of the data and a return to the main program, a branch is made to the previously set up address of the first instruction in the TND1 subroutine (FIG. 23B). Before the new trend data can be displayed, the display and keyboard logic must be set in state S2. Accordingly a 000 code is transmitted on data output conductors OUT 13, OUT 14 and OUT 15 to force the system into state S2 (see FIG. 4). The system then sets up the display interface for a "write" operation. As in the case of the "writing" of ECG data, data is not actually written on a disk. The disk interface is set up to control a write operation on disk drive "E", but all that it really does is to transmit 4,096 bits of data to the display and keyboard logic. But before the "writing" begins, a return address at TNDRET is set up. The "writing" operation is then begun.

After the 4.096 data bits have been transmitted to the display and keyboard logic, a return is made to the main program at which time a branch is taken to point TNDRET in the display service subroutine of FIG. 21A.

The display service routine is executed in the usual manner. It is necessary that the system be in state S3 in order to load ECG data. But it is not necessary to transmit the code for forcing this state because the display and keyboard logic always cycles to state S3 after the trend data loading operation is completed. Nor is it necessary to check if the cursor position is past position 256 on the screen; the cursor position is always reset to the left side of the screen when counter 50 (FIG. 4) is cleared when the system first enters state S2. The first operations performed at the TNDRET location on FIG. 21A are the setting of NEWCP to 1 (since the cursor position is new), and the updating of CRSPOS to the new value (corresponding to the first screen position).

Recording Sequence

There are many different ways to store data for each patient on the various sectors of a disk, which methods will be apparent to those skilled in the art. A specific technique for recording the data on the disk per se is not part of the present invention. However, one recording method will be described briefly.

A system such as that disclosed in my above-identified application Ser. No. 192,191 filed on Oct. 26, 1971 and which matured into U.S. Pat. No. 3,807,392, includes means for taking an ECG sample for each of several patients at a periodic rate, and for detecting ectopic beats and characterizing the ECG waveforms. In the case of eight patients, where the ECG signal of each patient is sampled 120 times per second, the overall sampling rate is 960 per second. Each sample is accompanied with a number representing the patient whose sample it is.

For each patient, a 480 8-bit word "circular" core buffer is provided. Successive 8-bit ECG samples are stored in successive locations in the buffer. Following the storage of a sample in the last location of a buffer, the next sample for the respective patient is stored in the first location of the buffer and the cycle then continues in this manner. A pointer word is used to reference the next location in the buffer into which the next sample is to be stored, the pointer word being up-dated following the storge of each sample.

Since the samples for each patient are taken at a rate of 120 per second, and there are 480 bytes in each core buffer, it is apparent that each buffer can store the samples representative of a 4-second segment of the respective patient's ECG signal. The samples are analyzed as they are taken, as disclosed in my above-identified applications, in order to detect an ectopic beat. Following the detection of such a beat, another 240 samples are taken and stored. In this manner, after two seconds have elapsed following the detection of an ectopic beat, the core buffer contains samples of the ECG signal which occurred during both the two seconds preceeding the detection of the ectopic beat and the two seconds which followed it. The starting location within the buffer for the 4-second recording can be determined from the value of the pointer word for the respective patient when the last sample is stored.

Before the samples are transferred to the disk, they are first transferred to a 512-byte temporary core buffer. The samples are stored in this temporary buffer starting with location 33 and ending with location 512. Time-successive samples are stored in these locations of the temporary buffer, the pointer word for the respective patient being used to determine the starting point in the circular buffer of the 480-sample sequence. A 32-byte message is stored in the first 32 locations of the temporary buffer depending on the patient number, the time of day and the type of beat detected.

For each patient, the system maintains a number which points to the next sector on the disk into which the next 512-byte ECG data and message sequence is to be stored. In this manner, an entire sector on the disk can be loaded by transferring to it the data contained in the temporary buffer. The storage of ECG and message data sequences in this manner for any patient ceases after his 256 disk sectors have been loaded.

It is also necessary to store the appropriate data in the patient's trend and table sectors on the disk (see FIG. 24). An internal clock notes the passage of each minute in real time. During each 1-minute interval, the system (e.g., the computer of FIG. 1) records the number of ectopic beats detected, and the number of overall beats detected.

To up-date the patient's trend sector, the value of the current minute can be used to determine the address within the sector in which the next entry is to be made. (This entry is a double one; ectopic beat and heartbeat rate values must be represented.) The entire sector should be cleared prior to recording. If an ectopic beat rate value is 0, no entry is made in the trend table. Otherwise, the appropriate ectopic beat rate value is stored together with the heartbeat rate value for the same minute.

Prior to the start of monitoring, each patient's table sector is cleared. To up-date the table sector, the system stores the address of the sector in which the first ECG signal segment for the current minute was stored. This sector address is stored in the table at the address corresponding to the current minute. If no waveforms were stored, no entry is made and a 0 remains at the respective location.

It should be noted that it is possible to design a system in which recording on the disk can proceed concurrently with the reading of data from the disk and its display. Of course, the display on the screen in such a case will be "incomplete"; since 0's are initially represented on the disk, the two trend plots have non-zero values only up to the current real time represented on the display. One of the main advantages of simultaneously recording on the disk and displaying its data is that the same computer can be used for both purposes at little additional cost.

Alternative Embodiments of The Invention

It will be apparent that the illustrative embodiment of the invention can be modified in many respects. For example, instead of allowing the physician to directly control movement of the curor, that can be left to the exclusive control of the computer. Each time that the cursor key is operated, the computer might be so informed and it would then transmit a cursor advance pulse (a 111 code on conductors OUT 13, OUT 14 and OUT 15), which pulse might then increment counter 50 to control advance of the cursor.

There is one alternative embodiment of the invention which is of particular interest. Instead of using a standard oscilloscope, a separate keyboard, and a specially designed display and keyboard logic (FIGS. 4–11) and display interface (FIG. 3), the invention can be implemented by using a computer, a disk drive with a standard interface, and a standard alphanumeric/graphics terminal such as the Beehive Model 5, equipped with option B for interfacing with the computer. This terminal is provided with four channels which can be used to display the two trend plots, an ECG waveform and an associated message. The unit is also provided with a cursor display and a full keyboard so that the physician commands can be interpreted by the computer.

The steps taken by the computer in such a system would be comparable to those described above. The Beehive terminal requires the transmission to it of a byte of data for each character in a message, or for each point in a plot, which is to be displayed. Following the transmission of each byte of data, a message is transmitted back to the computer to inform it that another byte can be transmitted. Thus one of the trend plots can be displayed by transmitting 256 bytes of data, followed by the transmission of another 256 bytes to control the display of the other trend plot. Whenever a new ECG waveform is to be displayed, 480 samples may be transmitted, followed by the transmission of 32 character codes. The disadvantage of such a system is that several seconds may be required to display an ECG waveform since the transmission speed is not as fast as that of the illustrative embodiment of the invention.

Thus the physician may be required to wait a few seconds following each operation of the display key before a new ECG waveform appears on the screen. The advantage of the system, of course, is that standard building blocks can be used; in particular, that is no need to build the special circuitry of FIGS.3–11.

Other variations are possible, even in the illustrative embodiment of the invention disclosed in detail above. For example, instead of providing a separate cursor display, it is possible to brighten a few successive bars in the histogram. Advances of the cursor in such a case would result in movement of the small bright part of the histogram. An another example, instead of displaying each successive recorded ECG waveform as the display key is operated, it is possible to display only those waveforms of a particular type, e.g., ventricular premature beats. In this case, the computer would continue to increment the value of ECGADR until it identified an ECG sector whose message characterizes the associated waveform as representing a VPB. As a further example, it is possible to have the system display successive waveforms going backward as well as forward in time (with the cursor moving to the left rather than the right on the screen). In this manner, the patients' history could be determined starting from the more recent waveforms, which are usually the most significant, and working backwards. By providing two pairs display and cursor keys, it would be possible to review a record in either direction.

Lastly, it is to be understood that the system of our invention is not limited to time-varying signals and events. In its broader aspects, the invention allows a particular point along the axis of one display to be selected, following which another display representing different information can be formed. For example, suppose that instead of the trend plots, there is displayed a demographic display of some type which depicts gross national product as a function of population. A statistician might then move the cursor along the population axis until he reached a population point along the axis for which the gross national product is of interest to him. On the disk there might be stored data for each country having the selected population and gross national product (within reasonable ranges). Successive operations of the display key might then control displays of a completely different type of information for each of successive countries within the selected group.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

What I claim is:

1. A method for displaying digital electronic data comprising the steps of:

a. representing the number of events that occur during each of succesive predetermined time intervals by a first set of data of a first type, said events being comprised of a plurality of sub-types of events which vary relative to each other by at least one identifiable characteristic b. representing each of said event sub-types according to said at least one identifiable characteristic by one respective set of data of a plurality of sets of data of a different second type, each of said event sub-types occurring during a time interval smaller than one of said predetermined time intervals;

c. forming a first graphic display of said first set of data in the form of a time plot;

d. selecting a point corresponding to one of said predetermined intervals along the time axis of said plot and visually identifying said selected point on said display;

e. selecting one of said sets of data of said second type which occurs during said selected predetermined intervals; and f. forming a second grahic display of said selected one of said sets of data of said second type as a function of time, whereby the event sub-type represented according to said at least one identifiable variable characteristic by said selected one of said sets of data of said second type is displayed.

2. The method of claim 1 wherein said events comprise ectopic heartbeats and said at least one identifiable variable characteristic is the magnitude-time relationship of ectopic heartbeats in an electrocardiographic waveform.

* * * * *